US011369571B2

(12) United States Patent
Diaz Quijano et al.

(10) Patent No.: US 11,369,571 B2
(45) Date of Patent: Jun. 28, 2022

(54) METHOD FOR THE PRODUCTION OF A DOSAGE FORM

(71) Applicant: OMYA INTERNATIONAL AG, Oftringen (CH)

(72) Inventors: Carolina Diaz Quijano, Oftringen (CH); Laura De Miguel, Oftringen (CH); Joachim Schölkopf, Oberkulm (CH)

(73) Assignee: OMYA INTERNATIONAL AG, Oftringen (CH)

( * ) Notice: Subject to any disclaimer, the term of this patent is extended or adjusted under 35 U.S.C. 154(b) by 0 days.

(21) Appl. No.: 16/310,491

(22) PCT Filed: Jun. 14, 2017

(86) PCT No.: PCT/EP2017/064552
§ 371 (c)(1),
(2) Date: Dec. 17, 2018

(87) PCT Pub. No.: WO2017/220406
PCT Pub. Date: Dec. 28, 2017

(65) Prior Publication Data
US 2019/0183801 A1      Jun. 20, 2019

Related U.S. Application Data

(60) Provisional application No. 62/355,401, filed on Jun. 28, 2016.

(30) Foreign Application Priority Data

Jun. 21, 2016   (EP) ..................... 16175595

(51) Int. Cl.
| | |
|---|---|
| A61K 9/16 | (2006.01) |
| A23L 27/00 | (2016.01) |
| A23L 33/10 | (2016.01) |
| A23L 33/16 | (2016.01) |
| A23P 10/20 | (2016.01) |
| A61K 8/02 | (2006.01) |
| A61K 8/19 | (2006.01) |
| A61K 9/20 | (2006.01) |
| A61K 31/085 | (2006.01) |
| A61K 31/192 | (2006.01) |
| A23K 20/10 | (2016.01) |
| A23K 40/10 | (2016.01) |
| A61Q 19/00 | (2006.01) |

(52) U.S. Cl.
CPC ............ *A61K 9/1611* (2013.01); *A23L 27/77* (2016.08); *A23L 33/10* (2016.08); *A23L 33/16* (2016.08); *A23P 10/20* (2016.08); *A61K 8/0225* (2013.01); *A61K 8/19* (2013.01); *A61K 9/1682* (2013.01); *A61K 9/2009* (2013.01); *A61K 31/085* (2013.01); *A61K 31/192* (2013.01); *A61Q 19/00* (2013.01); *A23K 20/10* (2016.05); *A23K 40/10* (2016.05); *A23V 2002/00* (2013.01); *A61K 2800/10* (2013.01); *A61K 2800/92* (2013.01)

(58) Field of Classification Search
CPC ......... A23K 20/10; A23K 40/10; A23L 27/77; A23L 33/10; A23L 33/16; A23P 10/20; A23V 2002/00; A61K 2800/10; A61K 2800/92; A61K 31/085; A61K 31/192; A61K 8/0225; A61K 8/19; A61K 9/1611; A61K 9/1682; A61K 9/2009; A61Q 19/00
See application file for complete search history.

(56) References Cited

U.S. PATENT DOCUMENTS

| | | | |
|---|---|---|---|
| 4,985,459 A | 1/1991 | Sunshine et al. | |
| 6,582,738 B2 | 6/2003 | Gubler | |
| 7,638,017 B2 | 12/2009 | Gane et al. | |
| 2003/0099741 A1 | 5/2003 | Gubler | |
| 2003/0157213 A1 | 8/2003 | Jenkins | |
| 2003/0206993 A1 | 11/2003 | Gubler | |
| 2004/0020410 A1 | 2/2004 | Gane et al. | |

FOREIGN PATENT DOCUMENTS

| | | |
|---|---|---|
| EP | 2 264 108 | 12/2010 |
| EP | 2 264 109 | 12/2010 |
| WO | 00/39222 | 7/2000 |
| WO | 2004/083316 | 9/2004 |
| WO | 2005/121257 | 12/2005 |
| WO | 2009/074492 | 6/2009 |
| WO | 2011/087629 | 7/2011 |
| WO | 2015/181306 | 12/2015 |
| WO | 2016/096997 | 6/2016 |

OTHER PUBLICATIONS

Barker, Karen; "Meet Narcan: The Amazing Drug that Helps Save Overdose Patients"; JEMS; Issue 8, vol. 33; 13 pages; published Jul. 31, 2008.*

(Continued)

*Primary Examiner* — Jeffrey T. Palenik
(74) *Attorney, Agent, or Firm* — Sheppard, Mullin, Richter & Hampton LLP

(57) ABSTRACT

A method is described for producing a dosage form and granules including surface-reacted calcium carbonate. Also described, are tablets and/or capsules obtained by the method. Methods using such a surface-reacted calcium carbonate, and a dosage form comprising the granules are also described. Further, methods of using the granules, or the tablets and/or capsules, or the dosage form in a pharmaceutical product, a nutraceutical product, an agricultural product, a cosmetic product, a home product, a food product, a packaging product and a personal care product are also described. A pharmaceutical product, a nutraceutical product, an agricultural product, a cosmetic product, a home product, a food product, a packaging product and a personal care product including the granules, or the tablets and/or capsules, or the dosage form are also described.

14 Claims, 4 Drawing Sheets

(56) References Cited

OTHER PUBLICATIONS

Stirnimann et al.; International Journal of Pharmaceutics; 466 (2014); pp. 266-275; published online Mar. 12, 2014.*
Stirnimann et al.; International Journal of Pharmaceutics; 466 (2014); pp. 266-275; published online Mar. 12, 2014. Improved copy for the record.*
Gane, Patrick A. C., Kettle, John P., Matthews, G. Peter and Ridgway, Cathy J., "Void Space Structure of Compressible Polymer Spheres and Consolidated Calcium Carbonate Paper-Coating Formulations", Industrial and Engineering Chemistry Research, vol. 35, No. 5, 1996, pp. 1753-1764.
Bacher, Camilla, Olsen, P. M., Bertelsen, Poul, Kristensen, J. and Sonnergaard, Jørn, "Improving the compaction properties of roller compacted calcium carbonate", International Journal of Pharmaceutics, vol. 342, No. 1-2, Sep. 2007, pp. 115-123.
International Search Report and Written Opinion dated Nov. 7, 2017 in corresponding International Patent Application No. PCT/EP2017/064552, filed Jun. 14, 2017, 11 pages.

\* cited by examiner

METHOD FOR THE PRODUCTION OF A DOSAGE FORM

CROSS-REFERENCE TO PRIOR APPLICATIONS

This application is a National Stage of PCT/EP2017/064552, filed Jun. 14, 2017, and designating the United States (published on Dec. 28, 2017, as WO 2017/220406 A1), which claims priority under 35 U.S.C. § 119 to European Patent Application No. 16175595.4, filed Jun. 21, 2016, and under 35 U.S.C. § 120 to Provisional Application No. 62/355,401, filed Jun. 28, 2016, each hereby expressly incorporated by reference in its entirety and each assigned to the assignee hereof.

The present invention relates to a method for producing a dosage form, granules consisting of surface reacted calcium carbonate, and tablets and/or capsules obtained by the method, the use of a surface-reacted calcium carbonate in a such a method, a dosage form comprising the granules, the use of the granules, or the tablets and/or capsules, or the dosage form in a pharmaceutical, nutraceutical, agricultural cosmetic, home, food, packaging and personal care product as well as a pharmaceutical, nutraceutical, agricultural, cosmetic, home, food, packaging and personal care product comprising the granules, or the tablets and/or capsules, or the dosage form.

Surface-reacted calcium carbonate powder can be used as a carrier in a great variety of applications due to its high porosity and capacity of loading active/inactive agents. Thus, surface-reacted calcium carbonate is gaining more and more importance in the production of dosage forms. Depending on the final use, the carrier material or matrix for such dosage forms needs to be first mixed with the required active ingredient or inactive precursor material and compatible formulating aid(s) needs to be found in order to be able to produce the dosage form. Such dosage forms are mainly manufactured out of powders. However, a frequent problem arising for such powders is that they are not free flowing, have low bulk density and generate too much dust. Thus, methods have been developed for producing dosage forms which are in form of a compacted material comprising surface-reacted calcium carbonate and avoiding the foregoing disadvantages.

For examples, unpublished European patent application EP 15 160 194.5 refers to a method for producing a dispersible dosage form, comprising the steps of: a) providing a functionalized calcium carbonate-comprising material, which is a reaction product of natural ground or precipitated calcium carbonate with carbon dioxide and one or more acids in an aqueous medium, wherein the carbon dioxide is formed in situ by the acid treatment and/or is supplied from an external source, b) providing at least one disintegrant; c) optionally providing at least one further formulating aid; d) mixing the functionalised calcium carbonate-comprising material of step a), the at least one disintegrant of step b) and the optionally at least one further formulating aid of step c); and e) compacting the mixture obtained in step d) by means of a roller compactor at a compaction pressure in the range from 2 to 20 bar into a ribbon; and f) milling the ribbon of step e) into granules, g) sieving of the granules of step f) by at least one mesh size.

Unpublished European patent application EP 14 199 037.4 refers to a method for producing a pharmaceutical delivery system, comprising the steps of: a) providing surface-reacted calcium carbonate, which is a reaction product of natural ground or precipitated calcium carbonate with carbon dioxide and one or more acids in an aqueous medium, wherein the carbon dioxide is formed in situ by the acid treatment and/or is supplied from an external source; b) providing at least one pharmaceutically active agent or pharmaceutically inactive precursor thereof; c) providing at least one formulating aid; d) mixing the surface-reacted calcium carbonate of step a), the at least one pharmaceutically active agent or pharmaceutically inactive precursor thereof of step b) and the at least one formulating aid of step c); and e) compacting the mixture obtained in step d) by means of a roller compacter at a compaction pressure in the range from 4 to 20 bar; and f) compacting the roller compacted mixture obtained in step e) for obtaining the pharmaceutical delivery system.

Unpublished European patent application EP 15 197 395.5 refers to a method for the production of granules comprising surface-reacted calcium carbonate, characterized by the steps of a) providing surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source; b) providing one or more active ingredient(s) in liquid form, c) saturating the surface-reacted calcium carbonate with the one or more active ingredient(s) in liquid form, d) providing one or more binder, and e) combining the saturated surface-reacted calcium carbonate obtained in step c) with the one or more binder of step d) under agitation in an agitation device.

However, also the methods described in the foregoing documents require the use of formulating aid(s) such as binder(s) and/or disintegrant(s) during compacting which need(s) to be compatible with the surface-reacted calcium carbonate powder as well as the active agent used, and further must be suitable for the desired end use, e.g. must be approved for human and/or animal consumption.

Thus, there is a continuous need for dosage forms and methods for their production which provide the same or even better performance than existing dosage forms and especially allows for producing a dosage form which is compacted in the absence of formulating aid(s) such as binder(s) and/or disintegrant(s). Furthermore, it is desired that the method allows for producing a dosage form having improved flowability, loose bulk- and tapped bulk-density, compared to the powder they have been made of, and are significantly less or almost non-dusting and thus can be easily be used in the further processing. In addition thereto, it is desired to provide a method for producing the dosage form which is efficient and allows for sufficient compacting of the dosage form.

It is thus an object of the present invention to provide a method for producing a dosage form. Another object may also be seen in the provision of a highly efficient compacting method for producing a dosage form. A further object may be seen in the provision of a method for producing a dosage form which is compacted in the absence of formulating aid(s) such as binder(s) and/or disintegrant(s). Another object may be seen in the provision of a method for producing a dosage form having improved flowability, loose bulk- and tapped bulk-density, compared to the powder they have been made of, and are significantly less or almost non-dusting and thus can be easily be used in the further processing.

One or more of the foregoing and other problems are solved by the subject-matter as defined herein in the independent claims. Advantageous embodiments of the present invention are defined in the corresponding sub-claims.

A first aspect of the present invention relates to a method for producing a dosage form. The method comprising the steps of:
a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
b) compacting the surface-reacted calcium carbonate of step a) by means of a roller compacter at a compaction pressure in the range from 1 to 30 kN/cm into a compacted form;
c) milling the compacted form of step b) into granules;
wherein the compacted form obtained in step b) consists of the surface-reacted calcium carbonate of step a).

According to another aspect of the present invention, granules consisting of surface reacted calcium carbonate as defined herein and optionally mixed with at least one formulating aid as defined herein and/or loaded with at least one active ingredient and/or inactive precursor thereof as defined herein are provided. According to a further aspect of the present invention, tablets and/or capsules obtained by the method as defined herein are provided.

According to a still further aspect of the present invention, a dosage form, preferably a tablet, mini-tablet or capsule, comprising the granules, as defined herein, is provided.

According to still another aspect of the present invention, the use of the granules as defined herein, or the tablets and/or capsules as defined herein, or the dosage form as defined herein in a pharmaceutical, nutraceutical, agricultural, cosmetic, home, food, packaging and personal care product is provided.

According to a further aspect of the present invention, a pharmaceutical, nutraceutical, agricultural, cosmetic, home, food, packaging and personal care product comprising the granules as defined herein, or the tablets and/or capsules as defined herein, or the dosage form as defined herein, is provided.

According to another aspect of the present invention, the use of a surface-reacted calcium carbonate in a method as defined herein, is provided.

According to one embodiment of the present method, the natural ground calcium carbonate is selected from calcium carbonate containing minerals selected from the group comprising marble, chalk, dolomite, limestone and mixtures thereof; or the precipitated calcium carbonate is selected from the group comprising precipitated calcium carbonates having aragonitic, vateritic or calcitic mineralogical crystal forms and mixtures thereof.

According to another embodiment of the present method, the surface-reacted calcium carbonate a) has a BET specific surface area of from 20 $m^2/g$ to 450 $m^2/g$, preferably from 20 $m^2/g$ to 250 $m^2/g$, more preferably from 30 $m^2/g$ to 160 $m^2/g$, most preferably from 40 $m^2/g$ to 150 $m^2/g$, still more preferably from 40 $m^2/g$ to 140 $m^2/g$ measured using the nitrogen and BET method according to ISO 9277; and/or b) comprises particles having a volume median grain diameter $d_{50}$ of from 1 µm to 50 µm, preferably from 1 to 45 µm, more preferably from 2 to 30 µm, even more preferably from 3 to 15 µm, and most preferably from 4 to 12 µm; and/or c) has an intra-particle intruded specific pore volume within the range of 0.15 to 1.35 $cm^3/g$, preferably of 0.30 to 1.30 $cm^3/g$, and most preferably of 0.40 to 1.25 $cm^3/g$, calculated from a mercury intrusion porosimetry measurement.

According to yet another embodiment of the present method, roller compacting step b) is carried out at a roller compaction pressure in the range from 1 to 28 kN/cm, more preferably in the range from 1 to 20 kN/cm and most preferably in the range from 2 to 10 kN/cm.

According to one embodiment of the present method, the method further comprising a step d) of sieving the granules of step c) by at least one mesh size.

According to another embodiment of the present method, sieving step d) is carried out by sieving on two or more different mesh sizes, preferably with mesh sizes of 90 µm, 180 µm, 250 µm, 355 µm, 500 µm and 710 µm.

According to yet another embodiment of the present method, the method further comprising a step e1) of mixing the compacted form obtained in step b) or the granules obtained in step c) and/or, if present, step d) with at least one formulating aid.

According to one embodiment of the present method, the at least one formulating aid is selected from the group comprising a disintegrant, preferably selected form the group comprising modified cellulose gums, insoluble crosslinked polyvinylpyrrolidones, starch glycolates, micro crystalline cellulose, pregelatinized starch, sodium carboxymethyl starch, low-substituted hydroxypropyl cellulose, homopolymers of N-vinyl-2-pyrrolidone, alkyl-, hydroxyalkyl-, carboxyalkyl-cellulose esters, alginates, microcrystalline cellulose and its polymorphic forms, ion exchange resins, gums, chitin, chitosan, clays, gellan gum, crosslinked polacrillin copolymers, agar, gelatine, dextrines, acrylic acid polymers, carboxymethylcellulose sodium/calcium, hydroxpropyl methyl cellulose phthalate, shellac or mixtures thereof, lubricants, especially an inner-phase lubricant and/or an outer-phase lubricant, impact modifiers, plasticizers, waxes, stabilizers, pigments, coloring agents, scenting agents, taste masking agents, flavoring agents, sweeteners, mouth-feel improvers, diluents, film forming agents, adhesives, buffers, adsorbents, odour-masking agents and mixtures thereof.

According to another embodiment of the present method, the method further comprising a step e2) of loading the compacted form obtained in step b) or the granules obtained in step c), if present, step d) with at least one active ingredient and/or inactive precursor thereof for obtaining loaded granules.

According to yet another embodiment of the present method, the at least one active ingredient and/or inactive precursor thereof is selected from the group comprising fragrances, flavours, herbal extracts, fruit extracts, nutrients, trace minerals, repellents, food, cosmetics, flame retardants, enzymes, macromolecules, pesticides, fertilizers, preserving agents, antioxidants, reactive chemicals, pharmaceutically active agents or pharmaceutically inactive precursors of synthetic origin, semi-synthetic origin, natural origin thereof, and mixtures thereof.

According to one embodiment of the present method, the at least one active ingredient and/or inactive precursor thereof is in liquid form, preferably the at least one active ingredient and/or inactive precursor thereof is provided in a solvent, preferably the solvent is selected from the group comprising water, methanol, ethanol, n-butanol, isopropanol, n-propanol, n-octanol, acetone, dimethylsulphoxide, dimethylformamide, tetrahydrofurane, vegetable oils and the derivatives thereof, animal oils and the derivatives thereof, molten fats and waxes, and mixtures thereof, and more preferably the solvent is water, ethanol and/or acetone.

According to another embodiment of the present method, loading step e2) is carried out by spraying or dropping the at least one active ingredient and/or inactive precursor thereof onto the compacted form obtained in step b) or the granules obtained in step c) or, if present, step d) and mixing it in a device selected from the group comprising fluidized bed dryers/granulators, ploughshare mixer, vertical or horizontal mixers, high or low shear mixer and high speed blenders.

According to yet another embodiment of the present method, the method further comprising a final step f) of tableting the loaded granules obtained in step e2) or filling the loaded granules obtained in step e2) into capsules.

It should be understood that for the purpose of the present invention the following terms have the following meaning.

For the purpose of the present invention, an "acid" is defined as Brønsted-Lowry acid, that is to say, it is an $H_3O^+$ ion provider. An "acid salt" is defined as an $H_3O^+$ ion-provider, e.g., a hydrogen-containing salt, which is partially neutralised by an electropositive element. A "salt" is defined as an electrically neutral ionic compound formed from anions and cations. A "partially crystalline salt" is defined as a salt that, on XRD analysis, presents an essentially discrete diffraction pattern.

In accordance with the present invention, $pK_a$ is the symbol representing the acid dissociation constant associated with a given ionisable hydrogen in a given acid, and is indicative of the natural degree of dissociation of this hydrogen from this acid at equilibrium in water at a given temperature. Such $pK_a$ values may be found in reference textbooks such as Harris, D. C. "Quantitative Chemical Analysis: $3^{rd}$ Edition", 1991, W.H. Freeman & Co. (USA), ISBN 0-7167-2170-8.

A "surface-reacted calcium carbonate" is a material comprising calcium carbonate and a water insoluble, at least partially crystalline, non-carbonate calcium salt, preferably, extending from the surface of at least part of the calcium carbonate. The calcium ions forming said at least partially crystalline non-carbonate calcium salt originate largely from the starting calcium carbonate material that also serves to form the surface-reacted calcium carbonate core. Such salts may include $OH^-$ anions and/or crystal water.

In the meaning of the present invention "water-insoluble" materials are defined as materials which, when mixed with deionised water and filtered on a filter having a 0.2 μm pore size at 20° C. to recover the liquid filtrate, provide less than or equal to 0.1 g of recovered solid material following evaporation at 95 to 100° C. of 100 g of said liquid filtrate. "Water-soluble" materials are defined as materials leading to the recovery of greater than 0.1 g of recovered solid material following evaporation at 95 to 100° C. of 100 g of said liquid filtrate.

A "specific surface area (SSA)" of a calcium carbonate in the meaning of the present invention is defined as the surface area of the calcium carbonate divided by its mass. As used herein, the specific surface area is measured by nitrogen gas adsorption using the BET isotherm (ISO 9277:2010) and is specified in $m^2/g$.

It is appreciated that the term "at least one active ingredient and/or inactive precursor thereof" differs from formulating aid(s), i.e. the at least one active ingredient and/or inactive precursor thereof does not include, nor are they by themselves, binders, disintegrants, lubricants, impact modifiers, plasticizers, waxes, stabilizers, pigments, coloring agents, scenting agents, taste masking agents, flavoring agents, mouth-feel improvers, diluents, film forming agents, adhesives, buffers, adsorbents, odour-masking agents and mixtures thereof.

The term "compacting" in the meaning of the present invention means a reduction in volume and/or density and an increase of the granule hardness which is obtained under pressure.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This e.g. means that, unless the context clearly dictates otherwise, the term "obtained" does not mean to indicate that e.g. an embodiment must be obtained by e.g. the sequence of steps following the term "obtained" though such a limited understanding is always included by the terms "obtained" or "defined" as a preferred embodiment.

According to the present invention it has been found that a dosage form can be prepared by compacting surface-reacted calcium carbonate in the absence of formulating aids such as binders and/or disintegrants. The compacted surface-reacted calcium carbonate can then be loaded with at least one active ingredient and/or inactive precursor thereof. Furthermore, the dosage form produced has improved flowability, loose bulk- and tapped bulk-density, compared to the powder it is made of, and is significantly less or almost non-dusting and thus can be easily be used in the further processing. In addition thereto, the method provides the possibility of efficiently compacting the dosage form.

In the following, it is referred to further details of the present invention and especially the foregoing steps of the method for producing a dosage form.

Method Step a)

In step a) of the method of the present invention, surface-reacted calcium carbonate is provided.

The surface-reacted calcium carbonate is a reaction product of natural ground calcium carbonate or precipitated calcium carbonate with carbon dioxide and one or more $H_3O^+$ ion donors, wherein the carbon dioxide is formed in-situ by the $H_3O^+$ ion donors treatment and/or is supplied from an external source.

A $H_3O^+$ ion donor in the context of the present invention is a Brønsted acid and/or an acid salt.

An "acid salt" is defined as an $H_3O^+$ ion-provider, e.g., a hydrogen-containing salt, which is partially neutralised by an electropositive element. A "salt" is defined as an electrically neutral ionic compound formed from anions and cations. A "partially crystalline salt" is defined as a salt that, on XRD analysis, presents an essentially discrete diffraction pattern.

In a preferred embodiment of the invention the surface-reacted calcium carbonate is obtained by a process comprising the steps of: (a) providing a suspension of natural or precipitated calcium carbonate, (b) adding at least one acid having a $pK_a$ value of 0 or less at 20° C. or having a $pK_a$ value from 0 to 2.5 at 20° C. to the suspension of step a), and (c) treating the suspension of step (a) with carbon dioxide before, during or after step (b). According to another embodiment the surface-reacted calcium carbonate is obtained by a process comprising the steps of: (A) providing a natural or precipitated calcium carbonate, (B) providing at least one water-soluble acid, (C) providing gaseous $CO_2$, (D) contacting said natural or precipitated calcium carbonate of step (A) with the at least one acid of step (B) and with the $CO_2$ of step (C), characterised in that: (i) the at least one acid of step B) has a $pK_a$ of greater than 2.5 and less than or equal to 7 at 20° C., associated with the ionisation of its first available hydrogen, and a corresponding anion is formed on loss of this first available hydrogen capable of forming a water-soluble calcium salt, and (ii) following contacting the at least one acid with natural or precipitated calcium carbonate, at least one water-soluble salt, which in the case of a hydrogen-containing salt has a $pK_a$ of greater than 7 at 20° C., associated with the ionisation of the first available hydrogen, and the salt anion of which is capable of forming water-insoluble calcium salts, is additionally provided.

"Natural ground calcium carbonate" (GCC) (or "natural calcium carbonate") preferably is selected from calcium carbonate containing minerals selected from the group comprising marble, chalk, dolomite, limestone and mixtures thereof. Natural ground calcium carbonate may comprise further naturally occurring components such as magnesium carbonate, alumino silicate etc.

In general, the grinding of natural ground calcium carbonate may be a dry or wet grinding step and may be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the calcium carbonate containing mineral material comprises a wet ground calcium carbonate containing mineral material, the grinding step may be performed under conditions such that autogenous grinding takes place and/or by horizontal ball milling, and/or other such processes known to the skilled man. The wet processed natural ground calcium carbonate containing mineral material thus obtained may be washed and dewatered by well-known processes, e.g. by flocculation, filtration or forced evaporation prior to drying. The subsequent step of drying (if necessary) may be carried out in a single step such as spray drying, or in at least two steps. It is also common that such a mineral material undergoes a beneficiation step (such as a flotation, bleaching or magnetic separation step) to remove impurities.

"Precipitated calcium carbonate" (PCC) in the meaning of the present invention is a synthesized material, generally obtained by precipitation following reaction of carbon dioxide and calcium hydroxide in an aqueous environment or by precipitation of calcium and carbonate ions, for example $CaCl_2$) and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the precipitated calcium carbonate is precipitated calcium carbonate, preferably comprising aragonitic, vateritic or calcitic mineralogical crystal forms or mixtures thereof.

Precipitated calcium carbonate may be ground prior to the treatment with carbon dioxide and at least one $H_3O^+$ ion donor by the same means as used for grinding natural calcium carbonate as described above.

According to one embodiment of the present invention, the natural ground or precipitated calcium carbonate is in form of particles having a weight median particle size $d_{50}$ of 0.05 to 10.0 µm, preferably 0.2 to 5.0 µm, more preferably 0.4 to 3.0 µm, most preferably 0.6 to 1.2 µm, especially 0.7 µm. According to a further embodiment of the present invention, the natural ground or precipitated calcium carbonate is in form of particles having a top cut particle size $d_{98}$ of 0.15 to 55 µm, preferably 1 to 40 µm, more preferably 2 to 25 µm, most preferably 3 to 15 µm, especially 4 µm.

The natural ground and/or precipitated calcium carbonate may be used dry or suspended in water. Preferably, a corresponding slurry has a content of natural ground or precipitated calcium carbonate within the range of 1 wt.-% to 90 wt.-%, more preferably 3 wt.-% to 60 wt.-%, even more preferably 5 wt.-% to 40 wt.-%, and most preferably 10 wt.-% to 25 wt.-% based on the weight of the slurry.

The one or more $H_3O^+$ ion donor used for the preparation of surface reacted calcium carbonate may be any strong acid, medium-strong acid, or weak acid, or mixtures thereof, generating $H_3O^+$ ions under the preparation conditions. According to the present invention, the at least one $H_3O^+$ ion donor can also be an acidic salt, generating $H_3O^+$ ions under the preparation conditions.

According to one embodiment, the at least one $H_3O^+$ ion donor is a strong acid having a $pK_a$ of 0 or less at 20° C.

According to another embodiment, the at least one $H_3O^+$ ion donor is a medium-strong acid having a $pK_a$ value from 0 to 2.5 at 20° C. If the $pK_a$ at 20° C. is 0 or less, the acid is preferably selected from sulphuric acid, hydrochloric acid, or mixtures thereof. If the $pK_a$ at 20° C. is from 0 to 2.5, the $H_3O^+$ ion donor is preferably selected from $H_2SO_3$, $H_3PO_4$, oxalic acid, or mixtures thereof. The at least one $H_3O^+$ ion donor can also be an acidic salt, for example, $HSO_4^-$ or $H_2PO_4^-$, being at least partially neutralized by a corresponding cation such as $Li^+$, $Na^+$ or $K^+$, or $HPO_4^{2-}$, being at least partially neutralised by a corresponding cation such as $Li^+$, $Na^+$, $K^+$, $Mg^{2+}$ or $Ca^{2+}$. The at least one $H_3O^+$ ion donor can also be a mixture of one or more acids and one or more acidic salts.

According to still another embodiment, the at least one $H_3O^+$ ion donor is a weak acid having a $pK_a$ value of greater than 2.5 and less than or equal to 7, when measured at 20° C., associated with the ionisation of the first available hydrogen, and having a corresponding anion, which is capable of forming water-soluble calcium salts. Subsequently, at least one water-soluble salt, which in the case of a hydrogen-containing salt has a $pK_a$ of greater than 7, when measured at 20° C., associated with the ionisation of the first available hydrogen, and the salt anion of which is capable of forming water-insoluble calcium salts, is additionally provided. According to the preferred embodiment, the weak acid has a $pK_a$ value from greater than 2.5 to 5 at 20° C., and more preferably the weak acid is selected from the group consisting of acetic acid, formic acid, propanoic acid, and mixtures thereof. Exemplary cations of said water-soluble salt are selected from the group consisting of potassium, sodium, lithium and mixtures thereof. In a more preferred embodiment, said cation is sodium or potassium. Exemplary anions of said water-soluble salt are selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water-soluble salt addition may be performed dropwise or in one step. In the case of drop wise addition, this addition preferably takes place within a time period of 10 minutes. It is more preferred to add said salt in one step.

According to one embodiment of the present invention, the at least one $H_3O^+$ ion donor is selected from the group consisting of hydrochloric acid, sulphuric acid, sulphurous acid, phosphoric acid, citric acid, oxalic acid, acetic acid, formic acid, and mixtures thereof. Preferably the at least one $H_3O^+$ ion donor is selected from the group consisting of hydrochloric acid, sulphuric acid, sulphurous acid, phosphoric acid, oxalic acid, $H_2PO_4$, being at least partially neutralised by a corresponding cation such as $Li^+$, $Na^+$ or $K^+$, $HPO_4^{2-}$, being at least partially neutralised by a corresponding cation such as $Li^+$, $Na^+$, $K^+$, $Mg^+$, or $Ca^+$ and mixtures thereof, more preferably the at least one acid is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid.

The one or more $H_3O^+$ ion donor can be added to the suspension as a concentrated solution or a more diluted solution. Preferably, the molar ratio of the $H_3O^+$ ion donor to the natural or precipitated calcium carbonate is from 0.01 to 4, more preferably from 0.02 to 2, even more preferably 0.05 to 1 and most preferably 0.1 to 0.58.

As an alternative, it is also possible to add the $H_3O^+$ ion donor to the water before the natural ground or precipitated calcium carbonate is suspended.

In a next step, the natural ground or precipitated calcium carbonate is treated with carbon dioxide. If a strong acid such as sulphuric acid or hydrochloric acid is used for the $H_3O^+$ ion donor treatment of the natural ground or precipitated calcium carbonate, the carbon dioxide is automatically formed. Alternatively or additionally, the carbon dioxide can be supplied from an external source.

$H_3O^+$ ion donor treatment and treatment with carbon dioxide can be carried out simultaneously which is the case when a strong or medium-strong acid is used. It is also possible to carry out $H_3O^+$ ion donor treatment first, e.g. with a medium strong acid having a $pK_a$ in the range of 0 to 2.5 at 20° C., wherein carbon dioxide is formed in-situ, and thus, the carbon dioxide treatment will automatically be carried out simultaneously with the $H_3O^+$ ion donor treatment, followed by the additional treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably 1:0.05 to 1:5.

In a preferred embodiment, the $H_3O^+$ ion donor treatment step and/or the carbon dioxide treatment step are repeated at least once, more preferably several times. According to one embodiment, the at least one $H_3O^+$ ion donor is added over a time period of at least about 5 min, preferably at least about 10 min, typically from about 10 to about 20 min, more preferably about 30 min, even more preferably about 45 min, and sometimes about 1 h or more.

Subsequent to the $H_3O^+$ ion donor treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted natural or precipitated calcium carbonate as an aqueous suspension having a pH of greater than 6.0, preferably greater than 6.5, more preferably greater than 7.0, even more preferably greater than 7.5.

Further details about the preparation of the surface-reacted natural ground calcium carbonate are disclosed in WO 00/39222 A1, WO 2004/083316 A1, WO 2005/121257 A2, WO 2009/074492 A1, EP 2 264 108 A1, EP 2 264 109 A1 and US 2004/0020410 A1, the content of these references herewith being included in the present application.

Similarly, surface-reacted precipitated calcium carbonate is obtained. As can be taken in detail from WO 2009/074492 A1, surface-reacted precipitated calcium carbonate is obtained by contacting precipitated calcium carbonate with $H_3O^+$ ions and with anions being solubilized in an aqueous medium and being capable of forming water-insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilized calcium ions correspond to an excess of solubilized calcium ions relative to the solubilized calcium ions naturally generated on dissolution of precipitated calcium carbonate by $H_3O^+$ ions, where said $H_3O^+$ ions are provided solely in the form of a counterion to the anion, i.e. via the addition of the anion in the form of an acid or non-calcium acid salt, and in absence of any further calcium ion or calcium ion generating source.

Said excess solubilized calcium ions are preferably provided by the addition of a soluble neutral or acid calcium salt, or by the addition of an acid or a neutral or acid non-calcium salt which generates a soluble neutral or acid calcium salt in-situ.

Said $H_3O^+$ ions may be provided by the addition of an acid or an acid salt of said anion, or the addition of an acid or an acid salt which simultaneously serves to provide all or part of said excess solubilized calcium ions.

In a further preferred embodiment of the preparation of the surface-reacted natural ground or precipitated calcium carbonate, the natural ground or precipitated calcium carbonate is reacted with the acid and/or the carbon dioxide in the presence of at least one compound selected from the group consisting of silicate, silica, aluminium hydroxide, earth alkali aluminate such as sodium or potassium aluminate, magnesium oxide, or mixtures thereof. Preferably, the at least one silicate is selected from an aluminium silicate, a calcium silicate, or an earth alkali metal silicate. These components can be added to an aqueous suspension comprising the natural or precipitated calcium carbonate before adding the acid and/or carbon dioxide.

Alternatively, the silicate and/or silica and/or aluminium hydroxide and/or earth alkali aluminate and/or magnesium oxide component(s) can be added to the aqueous suspension of natural or precipitated calcium carbonate while the reaction of natural ground or precipitated calcium carbonate with an acid and carbon dioxide has already started. Further details about the preparation of the surface-reacted natural ground or precipitated calcium carbonate in the presence of at least one silicate and/or silica and/or aluminium hydroxide and/or earth alkali aluminate component(s) are disclosed in WO 2004/083316 A1, the content of this reference herewith being included in the present application.

The surface-reacted calcium carbonate can be kept in suspension, optionally further stabilised by a dispersant. Conventional dispersants known to the skilled person can be used. A preferred dispersant is comprised of polyacrylic acids and/or carboxymethylcelluloses.

Alternatively, the aqueous suspension described above can be dried, thereby obtaining the solid (i.e. dry or containing as little water that it is not in a fluid form) surface-reacted natural or precipitated calcium carbonate in the form of granules or a powder.

The surface reacted calcium carbonate may have different particle shapes, such as e.g. the shape of roses, golf balls and/or brains.

In a preferred embodiment, the surface-reacted calcium carbonate has a specific surface area of from 20 m$^2$/g to 450 m$^2$/g, preferably from 20 m$^2$/g to 250 m$^2$/g, more preferably from 30 m$^2$/g to 160 m$^2$/g, most preferably from 40 m$^2$/g to 150 m$^2$/g, still more preferably from 40 m$^2$/g to 140 m$^2$/g measured using the nitrogen and BET method according to ISO 9277. The BET specific surface area in the meaning of the present invention is defined as the surface area of the particles divided by the mass of the particles. As used therein the specific surface area is measured by adsorption using the BET isotherm (ISO 9277:2010) and is specified in m$^2$/g.

According to one embodiment, the surface-reacted calcium carbonate comprises particles having a volume median grain diameter $d_{50}$ (vol) of from 1 to 50 μm, preferably from 1 to 45 μm, more preferably from 2 to 30 μm, even more preferably from 3 to 15 μm, and most preferably from 4 to 12 μm.

It may furthermore be preferred that the surface-reacted calcium carbonate comprises particles having a grain diameter $d_{98}$ (vol) of less than or equal to 40.0 μm. preferably less than or equal to 30.0 μm, more preferably less than or equal to 25.0 μm, still more preferably of less than or equal to 20.0 μm, more preferably of less than or equal to 19.0 μm. Preferably, the surface-reacted calcium carbonate comprises particles having a grain diameter $d_{98}$ (vol) in the range of from 5.0 to 40 μm, preferably form 6 to 30 μm, more preferably form 7.0 to 25.0 μm, still more preferably of from 10.0 to 20.0 μm, more preferably of from 11.0 to 19.0 μm.

The value $d_x$ represents the diameter relative to which x % of the particles have diameters less than $d_x$. This means that the $d_{98}$ value is the particle size at which 98% of all particles are smaller. The $d_{98}$ value is also designated as "top cut". The $d_x$ values may be given in volume or weight percent. The $d_{50}$ (wt) value is thus the weight median particle size, i.e. 50 wt.-% of all grains are smaller than this particle size, and the $d_{50}$ (vol) value is the volume median particle size, i.e. 50 vol. % of all grains are smaller than this particle size.

Volume median grain diameter $d_{50}$ was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement are analysed using the Mie theory, with a particle refractive index of 1.57 and an absorption index of 0.005.

The weight median grain diameter is determined by the sedimentation method, which is an analysis of sedimentation behaviour in a gravimetric field. The measurement is made with a Sedigraph™ 5100 or 5120, Micromeritics Instrument Corporation. The method and the instrument are known to the skilled person and are commonly used to determine grain size of fillers and pigments. The measurement is carried out in an aqueous solution of 0.1 wt.-% $Na_4P_2O_7$. The samples were dispersed using a high speed stirrer and sonicated.

The processes and instruments are known to the skilled person and are commonly used to determine grain size of fillers and pigments.

The specific pore volume is measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 μm (~nm). The equilibration time used at each pressure step is 20 seconds. The sample material is sealed in a 5 cm$^3$ chamber powder penetrometer for analysis. The data are corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p 1753-1764).

The total pore volume seen in the cumulative intrusion data can be separated into two regions with the intrusion data from 214 μm down to about 1-4 μm showing the coarse packing of the sample between any agglomerate structures contributing strongly. Below these diameters lies the fine interparticle packing of the particles themselves. If they also have intraparticle pores, then this region appears bi modal, and by taking the specific pore volume intruded by mercury into pores finer than the modal turning point, i.e. finer than the bi-modal point of inflection, we thus define the specific intraparticle pore volume. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the interparticle pore region and the intraparticle pore region, if present. Knowing the intraparticle pore diameter range it is possible to subtract the remainder interparticle and interagglomerate pore volume from the total pore volume to deliver the desired pore volume of the internal pores alone in terms of the pore volume per unit mass (specific pore volume). The same principle of subtraction, of course, applies for isolating any of the other pore size regions of interest.

Preferably, the surface-reacted calcium carbonate has an intra-particle intruded specific pore volume in the range from 0.15 to 1.35 cm$^3$/g, preferably of 0.30 to 1.30 cm$^3$/g, and most preferably of 0.40 to 1.25 cm$^3$/g, calculated from mercury intrusion porosimetry measurement.

The pore diameter of the surface-reacted calcium carbonate preferably is in a range of from 4 to 500 nm, more preferably in a range of between 20 and 80 nm, especially from 30 to 70 nm, e.g. 50 nm determined by mercury porosimetry measurement.

The intra-particle pore size of the surface-reacted calcium carbonate preferably is in a range of from 0.004 to 1.6 μm, more preferably in a range of between 0.005 to 1.3 μm, especially preferably from 0.006 to 1.15 µm and most preferably of 0.007 to 1.0 µm, e.g. 0.004 to 0.51 µm determined by mercury porosimetry measurement.

According to a preferred embodiment the intra- and/or inter particle pores of the surface-reacted calcium carbonate provided in step a) are hollow and, therefore, the surface-reacted calcium carbonate of step a) is unloaded.

The surface-reacted calcium carbonate may be in the form of dust or powder and preferably in the form of powder.

Method Step b)

According to step b) of the instant method, the surface-reacted calcium carbonate of step a) is compacted by means of a roller compacter at a compaction pressure in the range from 1 to 30 kN/cm into a compacted form.

The term "roller compacting" refers to a process in which fine powders are forced between two counter rotating rolls and pressed into a compacted form such as a ribbon, needles and/or flakes.

For the purposes of the present invention, roller compacting can be carried out with any suitable roller compactor known to the skilled person. For example, roller compacting is carried out with a Fitzpatrick® Chilsonator CCS220 roller compactor of the Fitzpatrick Company, USA.

It is one requirement of the instant method that method step b) is carried out at a compaction pressure in the range from 1 to 30 kN/cm. Preferably, roller compacting step b) is carried out at a roller compaction pressure in the range from 1 to 28 kN/cm, more preferably in the range from 1 to 20 kN/cm and most preferably in the range from 2 to 10 kN/cm.

Additionally or alternatively, the feed rate and/or the roll speed during roller compacting step is/are adjusted such that a thickness of from 0.2 to 6 mm, preferably from 0.3 to 3 mm and more preferably from 0.4 to 1 mm for the compacted form is obtained. For example, the feed rate or the roll speed during roller compacting step d) is adjusted such that a thickness of from 0.2 to 6 mm, preferably from 0.3 to 3 mm and more preferably from 0.4 to 1 mm for the compacted form is obtained. Alternatively, the feed rate and the roll speed during roller compacting step d) are adjusted such that a thickness of from 0.2 to 6 mm, preferably from 0.3 to 3 mm and more preferably from 0.4 to 1 mm for the compacted form is obtained.

It is one advantage of the present method that the compacting of the surface-reacted calcium carbonate can be carried out in the absence of formulating aid(s) such as binder(s) and/or disintegrant(s).

Therefore, one specific requirement of the present invention is that the compacted form of the surface-reacted calcium carbonate obtained in step b) consists of the surface-reacted calcium carbonate of step a).

Method Step c)

According to step c) of the instant method, the compacted form obtained in step b) is milled into granules.

Milling is carried out with any conventional mill known to the skilled person. For example, milling is carried out with a FitzMill® from the Fitzpatrick Company, USA.

In one embodiment, the obtained granules of step c) have a median grain size of from 10 to 4 500 µm, preferably from 50 to 2 500 µm and more preferably from 100 to 1 200 µm; and still more preferably 180 to 710 µm.

Additionally or alternatively, the obtained granules of step c) have a BET specific surface area of from 20 $m^2/g$ to 450 $m^2/g$, preferably from 20 $m^2/g$ to 250 $m^2/g$, more preferably from 30 $m^2/g$ to 160 $m^2/g$, most preferably from 40 $m^2/g$ to 150 $m^2/g$, still more preferably from 40 $m^2/g$ to 140 $m^2/g$ measured using the nitrogen and BET method according to ISO 9277.

Additionally or alternatively, the obtained granules of step c) have a bulk density of from 0.1 to 0.9 g/mL, preferably from 0.2 to 0.8 g/mL, more preferably from 0.3 to 0.7 g/mL, most preferably from 0.4 to 0.6 g/mL.

Additionally or alternatively, the obtained granules of step c) have a tapped density of from 0.1 to 0.9 g/mL, preferably from 0.2 to 0.9 g/mL, more preferably from 0.3 to 0.8 g/mL, most preferably from 0.4 to 0.7 g/mL, still more preferably from 0.5 to 0.7 g/mL.

Additionally or alternatively, the obtained granules of step c) have a compressibility index of from 10 to 40, preferably from 12 to 35, more preferably from 14 to 32, most preferably from 14 to 30, still more preferably from 15 to 28.

Additionally or alternatively, the obtained granules of step c) have an angle of repose of from 10 to 80°, preferably from 15 to 75°, more preferably from 20 to 70°, most preferably from 30 to 65°, still more preferably from 35 to 60°.

Preferably, the obtained granules of step c) have i) a median grain size of from 10 to 4 500 µm, preferably from 50 to 2 500 µm and more preferably from 100 to 1 200 µm; and still more preferably 180 to 710 µm; and ii) a BET specific surface area of from 20 $m^2/g$ to 450 $m^2/g$, preferably from 20 $m^2/g$ to 250 $m^2/g$, more preferably from 30 $m^2/g$ to 160 $m^2/g$, most preferably from 40 $m^2/g$ to 150 $m^2/g$, still more preferably from 40 $m^2/g$ to 140 $m^2/g$ measured using the nitrogen and BET method according to ISO 9277; and iii) a bulk density of from 0.1 to 0.9 g/mL, preferably from 0.2 to 0.8 g/mL, more preferably from 0.3 to 0.7 g/mL, most preferably from 0.4 to 0.6 g/mL; and iv) a tapped density of from 0.1 to 0.9 g/mL, preferably from 0.2 to 0.9 g/mL, more preferably from 0.3 to 0.8 g/mL, most preferably from 0.4 to 0.7 g/mL, still more preferably from 0.5 to 0.7 g/mL; and v) a compressibility index of from 10 to 40, preferably from 12 to 35, more preferably from 14 to 32, most preferably from 14 to 30, still more preferably from 15 to 28; and vi) an angle of repose of from 10 to 80°, preferably from 15 to 75°, more preferably from 20 to 70°, most preferably from 30 to 65°, still more preferably from 35 to 60°.

Optional Method Steps

According to optional method step d) of the present invention, the granules obtained in step c) are submitted to at least on sieving step d) by at least one mesh size.

Such sieving can be carried out with any conventional sieving means known to the skilled person. The sieving can be carried out using one or more mesh sizes. Suitable mesh sizes are, but not limited to mesh sizes in the order of 90 µm, 180 µm, 250 µm, 355 µm, 500 µm and 710 µm.

The sieved granules, thus have a median grain size of from 180 to 710 µm obtained by sieving on different mesh sizes, preferably by sieving with mesh sizes in the order of 90 µm, 180 µm, 250 µm, 355 µm, 500 µm and 710 µm. More preferably, by sieving with mesh sizes in the order of 90 µm, 180 µm, 250 µm, 355 µm, 500 µm and 710 µm and combining the sieved granules such that granules having median grain sizes of less than 90 µm and more than 710 µm are excluded. For example, sieving is carried out with a Vibrating sieve tower of Vibro Retsch, Switzerland.

In one embodiment, the sieving is carried out using mesh sizes in the order of 180 µm, 250 µm, 355 µm, 500 µm and 710 µm.

The sieved granules, thus have a median grain size of from 180 to 710 µm obtained by sieving on different mesh sizes, preferably by sieving with mesh sizes in the order of 180 µm, 250 µm, 355 µm, 500 µm and 710 µm. More preferably, by sieving with mesh sizes in the order of 180 µm, 250 µm, 355 µm, 500 µm and 710 µm and combining the sieved granules such that granules having median grain sizes of less than 180 µm and more than 710 µm are excluded. For example, sieving is carried out with a Vibrating sieve tower of Vibro Retsch, Switzerland.

In an alternative embodiment, the sieving is carried out using mesh sizes in the order of 250 µm, 355 µm, 500 µm and 710 µm.

The sieved granules thus have a median grain size of from 250 to 710 µm obtained by sieving on different mesh sizes, preferably by sieving with mesh sizes in the order of 250 µm, 355 µm, 500 µm and 710 µm. More preferably, by sieving with mesh sizes in the order of 250 µm, 355 µm, 500 µm and 710 µm and combining the sieved granules such that granules having median grain sizes of less than 250 µm and more than 710 µm are excluded. For example, sieving is carried out with a Vibrating sieve tower of Vibro Retsch, Switzerland.

It lies within the understanding of the present invention that other mesh sizes and combination of other mesh sizes lie within the spirit of the present invention.

In this embodiment, the method for producing a dosage form comprises, preferably consists of, the steps of:
  a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
  b) compacting the surface-reacted calcium carbonate of step a) by means of a roller compacter at a compaction pressure in the range from 1 to 30 kN/cm into a compacted form;
  c) milling the compacted form of step b) into granules; and
  d) sieving of the granules of step c) by at least one mesh size;
  wherein the compacted form obtained in step b) consists of the surface-reacted calcium carbonate of step a).

As already outlined above, the compacted form of the surface-reacted calcium carbonate obtained in step c) is prepared in the absence of formulating aid(s) such as binder(s) and/or disintegrant(s).

However, the compacted form of the surface-reacted calcium carbonate obtained in step b) can be mixed with at least one formulating aid.

Thus, in one embodiment, the method further comprises a step e1) of mixing the granules obtained in step c) and/or, if present, step d) with at least one formulating aid. Preferably, the granules obtained in step d) are mixed with the at least one formulating aid in a mixing step e1).

Mixing step e1) can be carried out by mixing the granules obtained in step c) and/or, if present, step d) with the at least one formulating aid in any order to form a mixture.

For the purposes of the present invention, any suitable mixing means known in the art may be used for carrying out mixing step e1). However, mixing step e1) preferably takes place in a mixer and/or blender, preferably a mixer such as a tumbling mixer.

The expression "at least one" formulating aid means that the formulating aid comprises one or more formulating aid(s).

According to one embodiment of the present invention, the formulating aid comprises only one formulating aid.

According to another embodiment of the present invention, the formulating aid comprises a mixture of two or more formulating aids. For example, the formulating aid comprises a mixture of two or three formulating aids.

In one embodiment, the at least one formulating aid comprises only one formulating aid.

For example, the at least one formulating aid is selected from the group comprising disintegrants, lubricants, impact modifiers, plasticizers, waxes, stabilizers, pigments, coloring agents, scenting agents, taste masking agents, flavoring agents, sweeteners, mouth-feel improvers, diluents, film forming agents, adhesives, buffers, adsorbents, odour-masking agents and mixtures thereof. In one embodiment, the at least one formulating aid may be also a binder.

It lies within the understanding of the skilled person that the mentioned formulating aid(s) are of mere illustrative character and are not intended to be of limiting character.

Preferably, the at least one formulating aid is a disintegrant selected form the group comprising modified cellulose gums, insoluble cross-linked polyvinylpyrrolidones, starch glycolates, micro crystalline cellulose, pregelatinized starch, sodium carboxymethyl starch, low-substituted hydroxypropyl cellulose, homopolymers of N-vinyl-2-pyrrolidone, alkyl-,hydroxyalkyl-, carboxyalkyl-cellulose esters, alginates, microcrystalline cellulose and its polymorphic forms, ion exchange resins, gums, chitin, chitosan, clays, gellan gum, crosslinked polacrillin copolymers, agar, gelatine, dextrines, acrylic acid polymers, carboxymethylcellulose sodium/calcium, hydroxpropyl methyl cellulose phtalate, shellac or mixtures thereof.

Examples of suitable disintegrants are: Ac-Di-Sol®, FMC, USA—which is a modified cellulose gum; Kollidon®CL, BASF, Germany—which is an insoluble crosslinked polyvinlypyrrolidone; Vivastar®, JRS, Germany—which is a sodium starch glycolate; MCC Polymorph II (MCC SANAQ Burst®)—Pharmatrans Sanaq AG, Switzerland—which is a stable crystal polymorph type II of Microcrystalline cellulose, MCC SANAQ 102 as standard microcrystalline cellulose (MCC).

In one embodiment, the at least one formulating aid is a lubricant, especially an inner-phase lubricant and/or outer-phase lubricant, preferably at least one outer-phase lubricant. Alternatively, the at least one formulating aid is at least one inner-phase lubricant and outer-phase lubricant.

Said at least one inner-phase lubricant can be selected from the group comprising sorbitan esters of fatty acids and polyoxyethylated hydrogenated castor oil (e.g. the product sold under the trade name CREMOPHOR®), block copolymers of ethylene oxide and propylene oxide (e.g. products sold under trade names PLURONIC® and POLOXAMER), polyoxyethylene fatty alcohol ethers, polyoxyethylene sorbitan fatty acid esters, sorbitan esters of fatty acids and polyoxyethylene steraric acid esters, stearyl alcohol, glycerol dibehenate, sodium stearyl fumarate, glycerol distearate and combinations thereof. Preferably, said at least one inner-phase lubricant is sodium stearyl fumarate.

Said at least one outer-phase lubricant can be selected from the group comprising lecithin, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllactylate, sodium stearoyl fumarate, magnesium and/or calcium stearate, hydrogenated vegetable oils, stearic acid, sodium lauryl sulphate, magnesium lauryl sulphate, colloidal silica, talc and combinations thereof. Preferably, said at least one outer-phase lubricant is magnesium and/or calcium stearate, more preferably magnesium stearate.

In one embodiment, the at least one formulating aid is a plasticizer. For example, the plasticizer can be a citrate-based plasticizer selected from the group consisting in triethyl citrate (TEC), tributyl citrate (TBC), acetyl tributyl citrate (ATBC), acetyl triethyl citrate (ATEC) and acetyl tri 2-ethyl-hexyl citrate (ATEHC).

According to a further embodiment, the at least one formulating aid may be further selected from diluents, film forming agents, adhesives, buffers, adsorbents, natural or synthetic scenting agents, natural or synthetic flavouring agents, natural or synthetic coloring agents, natural or synthetic sweeteners, natural or synthetic odour-masking agents, natural or synthetic flavouring- or taste-masking agents, natural and/or synthetic mouthfeel improvers and mixtures thereof.

Suitable natural or synthetic scenting agents include one or more volatilized chemical compounds, generally at a very low concentration, that humans or other animals perceive by the sense of olfaction.

Suitable natural or synthetic flavoring agents include but are not limited to mints, such as peppermint, menthol, vanilla, cinnamon, various fruit flavors, both individual or mixed, essential oils such as thymol, eucalyptol, menthol, and methyl salicylate, allylpyrazine, methoxypyrazines, 2-isobutyl-3 methoxypyrazine, acetyl-L-pyrazines, 2-acetoxy pyrazine, aldehydes, alcohols, esters, ketones, pyrazines, phenolics, terpenoids and mixtures thereof.

The flavoring agents are generally utilized in amounts that will vary depending upon the individual flavor, and may, for example, range in amount of about 0.5% to about 4% by weight of the final dosage form.

Suitable natural or synthetic coloring agents include, but are not limited to, titanium dioxide, flavone dyes, isoquinoline dyes, polyene colorants, pyran colorants, naphthochinone dyes, chinone and anthrachinone dyes, chromene dyes, benzophyrone dyes as well as indigoid dyes and indole colorants. Examples thereof are caramel coloring, annatto, chlorophyllin, cochineal, betanin, turmeric, saffron, paprika, lycopene, pandan and butterfly pea.

Suitable natural or synthetic sweeteners include but are not limited to xylose, ribose, glucose, mannose, galactose, fructose, dextrose, sucrose, sugar, maltose, partially hydrolyzed starch, or corn syrup solid, and sugar alcohols such as sorbitol, xylitol, mannitol, and mixtures thereof water soluble artificial sweeteners such as the soluble saccharin salts, i.e. sodium, or calcium saccharin salts, cyclamate salts, acesulfam-K and the like, and the free acid form of saccharin and aspartame based sweeteners such as L-aspartyl-phenylalanine methyl ester, Alitame® or Neotame®.

In general, the amount of sweetener will vary with the desired amount of sweeteners selected for a particular dosage form composition.

Suitable natural and/or synthetic mouthfeel improvers comprise but are not limited to polyethylenoxide (PEO-1NF), provided by Sumitomo Seika, Osaka, Lot.L20141017A, Hydroxylpropylcellulose (L-HPC LH-11), Shin-Etsu, Japan, Lot.505200, Hydroxypropylethylcellulose (Methocel E15 LV Premium EP), Lot. LD250012N23, Gummi arabicum Pheur, Roth, Germany, Lot.024208213, or Instant gum AA, Nexira, France or combinations thereof.

In one embodiment, the at least one formulating aid is provided in a total amount from about 0.1 wt.-% to about 99.0 wt.-%, preferably from about 0.3 wt.-% to about 50.0 wt.-%, even more preferably from about 0.3 wt.-% to about 10.0 wt.-%, still more preferably from about 0.3 wt.-% to about 5.0 wt.-%, and most preferably from about 0.5 wt.-% to about 2.5 wt.-% based on the total weight of the surface-reacted calcium carbonate of step a).

If the method comprises the provision of at last one formulating aid, the method for producing a dosage form comprises, preferably consists of, the steps of:
a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
b) compacting the surface-reacted calcium carbonate of step a) by means of a roller compacter at a compaction pressure in the range from 1 to 30 kN/cm into a compacted form;
c) milling the compacted form of step b) into granules; and
e1) mixing the granules obtained in step c) with at least one formulating aid;
wherein the compacted form obtained in step b) consists of the surface-reacted calcium carbonate of step a).

If the method further comprises a sieving, the method for producing a dosage form comprises, preferably consists of, the steps of:
a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
b) compacting the surface-reacted calcium carbonate of step a) by means of a roller compacter at a compaction pressure in the range from 1 to 30 kN/cm into a compacted form;
c) milling the compacted form of step b) into granules;
d) sieving of the granules of step c) by at least one mesh size; and
e1) mixing the granules obtained in step d) with at least one formulating aid;
wherein the compacted form obtained in step b) consists of the surface-reacted calcium carbonate of step a).

Additionally or alternatively, the compacted form of the surface-reacted calcium carbonate obtained in step b) or the granules obtained in step c) or, if present, step d) can be loaded with at least one active ingredient and/or inactive precursor thereof.

Thus, in one embodiment, the method further comprises a step e2) of loading the compacted form obtained in step b) or the granules obtained in step c) or, if present, step d) with the at least one active ingredient and/or inactive precursor thereof. Preferably, the granules obtained in step d) are loaded with the at least one active ingredient and/or inactive precursor thereof in loading step e2).

In one embodiment of the present invention, the at least one active ingredient and/or inactive precursor thereof comprises, preferably consists of, one active ingredient or inactive precursor thereof. Alternatively, the at least one active ingredient and/or inactive precursor thereof comprises, preferably consists of, two or more active ingredient(s) and/or inactive precursor(s) thereof. For example, the at least one active ingredient and/or inactive precursor thereof comprises, preferably consists of, two or three active ingredient(s) and/or inactive precursor(s) thereof.

Preferably, the at least one active ingredient and/or inactive precursor thereof comprises, preferably consists of, one active ingredient or inactive precursor thereof.

The term "active ingredient" in the meaning of the present invention refers to a substance having a specific effect in an organism and causing a specific reaction in humans, animals, microorganisms and/or plants.

It is appreciated that the at least one active ingredient and/or inactive precursor thereof may be a chiral compound. Thus, the at least one active ingredient and/or inactive precursor thereof encompasses the (R)-enantiomer, (S)-enantiomer and mixtures thereof, e.g. the racemic mixture.

Additionally or alternatively, the at least one active ingredient and/or inactive precursor thereof may be an isomeric compound. Thus, the at least one active ingredient and/or inactive precursor thereof encompasses the (Z)-isomer, (E)-isomer and mixtures thereof.

For example, the at least one active ingredient and/or inactive precursor thereof is selected from the group comprising fragrances, flavours, herbal extracts, fruit extracts, nutrients, trace minerals, repellents, food, cosmetics, flame retardants, enzymes, macromolecules, pesticides, fertilizers, preserving agents, antioxidants, reactive chemicals, pharmaceutically active agents or pharmaceutically inactive precursors of synthetic origin, semi-synthetic origin, natural origin thereof, and mixtures thereof.

Fragrances are preferably alcohols, aldehydes and/or ketones having a molecular weight of at least about 100 g/mol and which are useful in imparting an odour, fragrance, essence, or scent either alone or in combination with other fragrances. For example, the fragrance can be selected from the group comprising 2,4-dimethyl-3-cyclohexene-1-methanol (floralol), 2,4-dimethyl cyclohexane methanol (dihydro floralol), 5,6-dimethyl-1-methylethenylbicyclo[2.2.1]hept-5-ene-2-methanol (arbozol), α,α,-4-trimethyl-3-cyclohexen-1-methanol (α-terpineol), 2,4,6-trimethyl-3-cyclohexene-1-methanol (isocyclo geraniol), 4-(1-methylethyl)cyclohexane methanol (mayol), α-3,3-trimethyl-2-norborane methanol, 1,1-dimethyl-1-(4-methylcyclohex-3-enyl)methanol, 2-phenylethanol, 2-cyclohexyl ethanol, 2-(o-methylphenyl)-ethanol, 2-(m-methylphenyl)ethanol, 2-(p-methylphenyl)ethanol, 6,6-dimethylbicyclo-[3.1.1]hept-2-ene-2-ethanol (nopol), 2-(4-methylphenoxy)-ethanol, 3,3-dimethyl-Δ²-β-norbornane ethanol (patchomint), 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methyl-phenyl)ethanol, 1-phenylpropanol, 3-phenylpropanol, 2-phenylpropanol (Hydrotropic Alcohol), 2-(cyclododecyl)propan-1-ol (Hydroxy-ambran), 2,2-dimethyl-3-(3-methylphenyl)-propan-1-ol (Majantol), 2-methyl-3-phenylpropanol, 3-phenyl-2-propen-1-ol (cinnamyl alcohol), 2-methyl-3-phenyl-2-propen-1-ol(methyl-cinnamyl alcohol), α-n-pentyl-3-phenyl-2-propen-1-ol (α-amyl-cinnamyl alcohol), ethyl-3-hydroxy-3-phenyl propionate, 2-(4-methylphenyl)-2-propanol, 3-(4-methylcyclohex-3-ene)butanol, 2-methyl-4-(2,2,3-trimethyl-3-cyclopenten-1-yl)butanol, 2-ethyl-4-(2,2,3-trimethyl-cyclopent-3-enyl)-2-buten-1-ol, 3-methyl-2-buten-1-ol(prenol), 2-methyl-4-(2,2,3-trimethyl-3-cyclopenten-1-yl)-2-buten-1-ol, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)-butan-2-one, 3-methyl-pentanol, 3-methyl-3-penten-1-ol, 1-(2-propenyl) cyclopentan-1-ol (plinol), 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0.sup.(2,6)]hept-3-yl)-2-penten-1-ol(santalol), 4-methyl-1-phenyl-2-pentanol, 5-(2,2,3-trimethyl-3-cyclopentenyl)-3-methylpentan-2-ol (sandalore), (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexenol, cis-3-hexen-1-ol, trans-2-hexen-1-ol, 2-isoproenyl-4-methyl-4-hexen-1-ol (Lavandulol), 2-ethyl-2-prenyl-3-hexenol, 1-hydroxymethyl-4-iso-propenyl-1-cyclohexene (Dihydrocuminyl alcohol), 1-methyl-4-isopropenylcyclohex-6-en-2-ol (carvenol), 6-methyl-3-isopropenylcyclohexan-1-ol (dihydrocarveol), 1-methyl-4-iso-propenylcyclohexan-3-ol, 4-isopropyl-1-methylcyclohexan-3-ol, 4-tert-butylcyclohexanol, 2-tert-butylcyclohexanol, 2-tert-butyl-4-methylcyclohexanol (rootanol), 4-isopropyl-cyclohexanol, 4-methyl-1-(1-methylethyl)-3-cyclohexen-1-ol, 2-(5,6,6-trimethyl-2-norbornyl)cyclohexanol, isobornylcyclohexanol, 3,3,5-trimethylcyclohexanol, 1-methyl-4-isopropylcyclohexan-3-ol, 1-methyl-4-isopropylcyclohexan-8-ol (dihydroterpineol), 1,2-dimethyl-3-(1-methylethyl)cyclohexan-1-ol, heptanol, 2,4-dimethylheptan-1-ol, 6-heptyl-5-hepten-2-ol (isolinalool), 2,4-dimethyl-2,6-heptandienol, 6,6-dimethyl-2-oxymethyl-bicyclo[3.1.1]hept-2-ene (myrcenol), 4-methyl-2,4-heptadien-1-ol, 3,4,5,6,6-pentamethyl-2-heptanol, 3,6-dimethyl-3-vinyl-5-hepten-2-ol, 6,6-dimethyl-3-hydroxy-2-methylenebicyclo[3.1.1]heptane, 1,7,7-trimethylbicyclo[2.2.1]heptan-2-ol, 2,6-dimethylheptan-2-ol (dimetol), 2,6,6-trimethylbicyclo[1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol(geraniol), 3,7-dimethyl-2,6-octadien-1-ol (nerol), 3,7-dimethyl-7-methoxyoctan-2-ol(osyrol), 3,7-dimethyl-1,6-octadien-3-ol (linalool), 3,7-dimethyloctan-1-ol(pelargol), 3,7-dimethyl-octan-3-ol (tetrahydrolinalool), 2,4-octadien-1-ol, 3,7-dimethyl-6-octen-3-ol (dihydrolinalool), 2,6-dimethyl-7-octen-2-ol (dihydromyrcenol), 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyl-octan-3-ol, 2,6-dimethyl-7-octen-2-ol, 2,6-dimethyl-3,5-octadien-2-ol(muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6-nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linalool), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol (nerolidol), 3,7,11,15-tetramethylhexadec-2-en-1-ol (phytol), 3,7,11,15-tetramethylhexadec-1-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-iso-propylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydroxytoluene, 4-hydroxy-3-methoxybenzaldehyde, 2-ethoxy-4-hydroxybenzaldehyde, decahydro-2-naphthol, 2,5,5-trimethyl-octahydro-2-naphthol, 1,3,3-trimethyl-2-norbornanol(fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1H-inden-5-ol, 2-methyl-2-vinyl-5-(1-hydroxy-1-methylethyl)tetra-hydrofuran, β-caryophyllene alcohol, vanillin, ethyl vanillin, cinnamaldehyde, benzaldehyde, phenyl acetaldehyde, heptylaldehyde, octylaldehyde, decylaldehyde, undecylaldehyde, undecylenic aldehyde, dodecylaldehyde, tridecylaldehyde, methylnonyl aldehyde, didecylaldehyde, anisaldehyde, citronellal, citronellyloxyaldehyde, cyclamen aldehyde, α-hexyl cinnamaldehyde, hydroxycitronellal, α-methyl cinnamaldehyde, methylnonyl acetaldehyde, propylphenyl aldehyde, citral, perilla aldehyde, tolylaldehyde, tolylacetaldehyde, cuminaldehyde, LILIAL®, salicyl aldehyde, α-amylcinnamaldehyde and heliotropin and mixtures thereof.

Various essential oils, herbal extracts and/or fruit extracts may also be used, preferably those with various medicinal or dietary supplement properties. Essential oils, herbal extracts and/or fruit extracts are generally extracts or aromatic plants, plant parts, fruit or fruit parts that can be used medicinally or for flavouring. Suitable herbal extracts and/or fruit extracts can be used singly or in various mixtures.

Commonly used essential oils, herbal extracts and/or fruit extracts include Echinacea, Goldenseal, Calendula, Rosemary, Thyme, Kava Kava, Aloe, Blood Root, Grapefruit Seed Extract, Black Cohosh, Ginseng, Guarana, Cranberry, Ginko Biloba, St. John's Wort, Evening Primrose Oil, Yohimbe Bark, Green Tea, Ma Huang, Maca, Bilberry, Lutein, Ginger, eugenol-containing oils and combinations thereof.

A variety of nutrients may be used including virtually any vitamin, mineral and/or phytochemical. For example, vitamin A, vitamin B1, vitamin B6, vitamin B12, vitamin B2, vitamin B6, vitamin D, vitamin E, i.e. tocopheroles, vitamin K, thiamine, riboflavin, biotin, folic acid, niacin, pantothenic acid, Q10, alpha lipoic acid, dihydrolipoic acid, curcumin, xanthophylls, beta cryptoxanthin, lycopene, lutein, zeaxanthin, astaxanthin, beta-carotene, carotenes, mixed carotenoids, polyphenols, flavonoids, sodium, potassium, calcium, magnesium, sulphur, chlorine, choline, and/or phytochemicals such as carotenoids, chlorophyll, chlorophyllin, fibre, flavanoids, anthocyanins, cyaniding, delphinidin, malvidin, pelargonidin, peonidin, petunidin, flavanols, catechin, epicatechin, epigallocatechin, epigallocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof, may be used. Examples of nutrients that can be used as active ingredient(s) are set forth in U.S. Patent Application Publication Nos. 2003/0157213 A1, 2003/0206993 and 2003/0099741 A1 which are incorporated in their entirety herein by reference for all purposes.

In one embodiment, trace minerals can be used, e.g. manganese, zinc, copper, fluorine, molybdenum, iodine, cobalt, chromium, selenium, phosphorous, and combinations thereof.

Enzymes can include but are not limited to coenzyme Q10, pepsin, phytase, trypsin, lipases, proteases, cellulases, lactase and combinations thereof. Macromolecules are preferably known proteins, antibodies, receptors, carries, polypeptides, peptides, probiotics or lipids.

Pesticides are preferably any known herbicide, insecticide, insect growth regulator, nematicide, termiticide, molluscicide, piscicide, avicide, rodenticide, predacide, bactericide, insect repellent, animal repellent, antimicrobial, fungicide, disinfectant (antimicrobial), and sanitizer known to the skilled person.

It is to be noted that the preserving agent may be any such compound known to the skilled person. For example, preserving agents may include, but are not limited to, phenoxyethanol, ethylhexylglycerin, parabens such as methyl paraben, ethyl paraben, propyl paraben, butyl paraben and mixtures thereof, benzalkonium chloride, chlorbutanol, benzyl alcohol, cetylpyridinium chloride, tartaric acid, lactic acid, malic acid, acetic acid, benzoic acid, sodium benzoate, sorbic acid, potassium sorbate and mixtures thereof.

Antioxidants are preferably selected from the group comprising butylhydroxyanisol (BHA), butylhydroxytoluol (BHT), gallate, carotinoid, polyphenols such as resveratrol, flavonoid and mixtures thereof, derivatives of polyphenols, tocopherol and salts thereof, betacarotin, ubichinon, tocotrienol, dihydroquercetin, antioxidants of natural origin and mixtures thereof. If the antioxidant is of natural origin, the antioxidant can be e.g. a conifer extract, pinus pinaster bark extract such as Pycnogenol® from Horphag, Switzerland, and/or emblica officinalis fruit extract such as Saberry® from Sabinsa corporation, Germany.

The pharmaceutically active agent or pharmaceutically inactive precursor thereof is preferably selected from the group comprising pharmaceutically active agent or pharmaceutically inactive precursor of synthetic origin, semi-synthetic origin, natural origin and combinations thereof.

Thus, a pharmaceutically active agent refers to pharmaceutically active agents which are of synthetic origin, semi-synthetic origin, natural origin and combinations thereof. Further, a pharmaceutically inactive precursor of the pharmaceutically active agent refers to pharmaceutically inactive precursors which are of synthetic origin, semi-synthetic origin, natural origin and combinations thereof and will be activated at a later stage to the respective pharmaceutically active agent.

The conversion or activation of such pharmaceutically active or inactive prodrugs is known to the skilled person and commonly in use, e.g. conversion and activation in the stomach and/or gastro-intestinal pathway—such as for examples by ph-mediated or enzymatic-mediated activation.

It lies within the understanding of the skilled person that the mentioned activation methods are of mere illustrative character and are not intended to be of limiting character.

It is to be noted that the pharmaceutically active agent or pharmaceutically inactive precursor thereof, may be any such compound known to the skilled person.

Pharmaceutically active agents thus include any compound that provides prophylactic and/or therapeutic properties when administered to humans and/or animals. Examples include, but are not limited to, pharmaceutical actives, therapeutic actives, veterinarian actives, nutraceuticals, and growth regulators and the corresponding active or inactive precursor thereof.

For example, the pharmaceutically active agent or pharmaceutically inactive precursor thereof can be an anti-inflammatory agent. Such agents may include, but are not limited to, non-steroidal anti-inflammatory agents or NSAIDs, such as propionic acid derivatives; acetic acid derivatives; fenamic acid derivatives; biphenylcarboxylic acid derivatives; and oxicams. All of these NSAIDs are fully described in U.S. Pat. No. 4,985,459 to Sunshine et al., incorporated by reference herein in its entirety as to the description of such NSAIDs. Examples of useful NSAIDs include acetylsalicylic acid, ibuprofen, naproxen, benoxaprofen, flurbiprofen, fenoprofen, fenbufen, ketoprofen, indoprofen, pirprofen, carprofen, oxaprozin, pranoprofen, microprofen, tioxaprofen, suprofen, alminoprofen, tiaprofenic acid, fluprofen, bucloxic acid and mixtures thereof.

Also useful are the steroidal anti-inflammatory drugs such as hydrocortisone and the like, and COX-2 inhibitors such as meloxicam, celecoxib, rofecoxib, valdecoxib, etoricoxib or mixtures thereof. Mixtures of any of the above anti-inflammatories may be used.

Other materials that can be used as pharmaceutically active agent or pharmaceutically inactive precursor thereof include commonly known mouth and throat products. These products include, but are not limited to, upper respiratory agents such as phenylephrine, diphenhydramine, dextromethorphan, bromhexine and chlorpheniramine, gastrointestinal agents such as famotidine, loperamide and simethicone, anti-fungals such as miconazole nitrate, antibiotics and analgesics such as ketoprofen and fluribuprofen.

The at least one pharmaceutically active agent or pharmaceutically inactive precursor thereof may be an anti-tartar agent. Anti-tartar agents useful herein include phosphates. Phosphates include pyrophosphates, polyphosphates, polyphosphonates and mixtures thereof. Pyrophosphates are among the best known phosphates for use in dental care products. Pyrophosphate ions delivered to the teeth derive from pyrophosphate salts. The pyrophosphate salts useful in the present pharmaceutical delivery system include the dialkali metal pyrophosphate salts, tetra-alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their non-hydrated as well as hydrated forms are preferred. Anticalculus phosphates include potassium and sodium pyrophosphates; sodium tripolyphosphate; diphosphonates, such as ethane-1-hydroxy-1,I-diphosphonate; 1-azacycloheptane-1,1-diphosphonate; and linear alkyl diphosphonates; linear carboxylic acids and sodium and zinc citrate.

The pharmaceutically active agent or pharmaceutically inactive precursor thereof may be also selected from sodium pyrosulphite, butylhydroxytoluene, butylated hydroxyanisole.

The pharmaceutically active agent or pharmaceutically inactive precursor thereof may be also selected from ephedrine, magaldrate, pseudoephedrine, sildenafil, xylocaine, benzalconium chloride, caffeine, phenylephrine, amfepramone, orlistat, sibutramine, acetaminophen, aspirin, glitazones, metformin, chlorpromazine, dimenhydrinat, domperidone, meclozine, metoclopramide, odansetron, prednisolone, promethazine, acrivastine, cetirizine, cinnarizine, clemastine, cyclizine, desloratadine, dexchlorpheniramine, dimenhydrinate, ebastine, fexofenadine, ibuprofen, levolevoproricin, loratadine, meclozine, mizolastine, promethazine, miconazole, chlorhexidine diacetate, fluoride, decapeptide KSL, aluminium fluoride, aminochelated calcium, ammonium fluoride, ammonium fluorosilicate, ammonium monofluorphosphate, calcium fluoride, calcium gluconate, calcium glycerophosphate, calcium lactate, calcium monofluorphosphate, calciumcarbonate, carbamide, cetyl pyridinium chloride, chlorhexidine, chlorhexidine digluconate, chlorhexidine chloride, chlorhexidine diacetate, CPP caseine phospho peptide, hexetedine, octadecentyl ammonium fluoride, potassium fluorosilicate, potassium chloride, potassium monofluorphosphate, sodium bi carbonate, sodium carbonate, sodium fluoride, sodium fluorosilicate, sodium monofluorphosphate, sodium tri polyphosphate, stannous fluoride, stearyl trihydroxyethyl propylenediamine dihydrofluoride, strontium chloride, tetra potassium pyrophosphate, tetra sodium pyrophosphate, tripotassium orthophosphate, trisodium orthophosphate, alginic acid, aluminium hydroxide, sodium bicarbonate, sildenafil, tadalafil, vardenafil, yohimbine, cimetidine, nizatidine, ranitidine, acetylsalicylic acid, clopidogrel, acetylcysteine, bromhexine, codeine, dextromethorphan, diphenhydramine, noscapine, phenylpropanolamine, vitamin D, simvastatin, bisacodyl, lactitol, lactulose, magnesium oxide, sodium picosulphate, senna glycosides, benzocaine, lidocaine, tetracaine, almotriptan, eletriptan, naratriptan, rizatriptan, sumatriptan, zolmitriptan, calcium, chromium, copper, iodine, magnesium, manganese, molybdenum, phosphor, selenium, zinc, chloramine, hydrogenperoxide, metronidazole, triamcinolonacetonide, benzethonium chl., cetyl pyrid. chl., chlorhexidine, fluoride, lidocaine, amphotericin, miconazole, nystatin, fish oil, Ginkgo biloba, ginseng, ginger, purple coneflower, saw palmetto, cetirizine, levocetirizine, loratadine, diclofenac, flurbiprofen, acrivastine pseudoephedrine, loratadine pseudoephedrine, glucosamine, hyaluronic acid, decapeptide KSL-W, decapeptide KSL, resveratrol, misoprostol, bupropion, ondansetron HCl, esomeprazole, lansoprazole, omeprazole, pantoprazole, rabeprazole, bacteria and the like, loperamide, simethicone, acetylsalicylic acid and others, sucralfate, clotrimazole, fluconazole, itraconazole, ketoconazole, terbinafine, allopurinol, probenecid, atorvastatin, fluvastatin, lovastatin, nicotinic acid, pravastatin, rosuvastatin, simvastatin, pilocarpine, naproxen, alendronate, etidronate, raloxifene, risedronate, benzodiazepines, disulphiram, naltrexone, buprenorphine, codeine, dextropropoxyphene, fentanyl, hydromorphone, ketobemidone, ketoprofen, methadone, morphine, naproxen, nicomorphine, oxycodone, pethidine, tramadol, amoxicillin, ampicillin, azithromycin, ciprofloxacin, clarithromycin, doxycyclin, erythromycin, fusidic acid, lymecycline, metronidazole, moxifloxacin, ofloxacin, oxytetracycline, phenoxymethylpenicillin, rifamycins, roxithromycin, sulphamethizole, tetracycline, trimethoprim, vancomycin, acarbose, glibenclamide, gliclazide, glimepiride, glipizide, insulin, repaglinide, tolbutamide, oseltamivir, aciclovir, famciclovir, penciclovir, valganciclovir, amlopidine, diltiazem, felodipine, nifedipine, verapamil, finasteride, minoxidil, cocaine, buphrenorphin, clonidine, methadone, naltrexone, calcium antagonists, clonidine, ergotamine, β-blockers, aceclofenac, celecoxib, dexiprofen, etodolac, indometacin, ketoprofen, ketorolac, lornoxicam, meloxicam, nabumetone, oiroxicam, parecoxib, phenylbutazone, piroxicam, tiaprofenic acid, tolfenamic acid, aripiprazole, chlorpromazine, chlorprothixene, clozapine, flupentixol, fluphenazine, haloperidol, lithium carbonate, lithium citrate, melperone, penfluridol, periciazine, perphenazine, pimozide, pipamperone, prochlorperazine, risperidone, thioridizin, fluconazole, itraconazole, ketoconazole, voriconazole, opium, benzodiazepines, hydroxine, meprobamate, phenothiazine, aluminiumaminoacetate, esomeprazole, famotidine, magnesium oxide, nizatide, omeprazole, pantoprazole, fluconazole, itraconazole, ketoconazole, metronidazole, amphetamine, atenolol, bisoprolol fumarate, metoprolol, metropolol, pindolol, propranolol, auranofin, and bendazac.

Further examples of useful pharmaceutically active agents or pharmaceutically inactive precursors thereof can include active ingredients selected from the therapeutical groups comprising: Analgesic, Anaesthetic, Antipyretic, Anti-allergic, Anti-arrhythmic, Appetite suppressant, Antifungal, Anti-inflammatory, Broncho dilator, Cardiovascular drugs, Coronary dilator, Cerebral dilator, Peripheral vasodilator, Anti-infective, Psychotropic, Anti-manic, Stimulant, Antihistamine, Laxative, Decongestant, Gastro-intestinal sedative, Sexual dysfunction agent, Disinfectants, Anti-diarrhoeal, Anti-anginal substance, Vasodilator, Anti-hypertensive agent, Vasoconstrictor, Migraine treating agent, Antibiotic, Tranquilizer, Antipsychotic, Anti-tumour drug, Anticoagulant, Antithrombotic agent, Hypnotic, Sedative, Anti-emetic, Anti-nauseant, Anticonvulsant, Neuromuscular agent, Hyper and hypoglycaemic, Thyroid and antithyroid, Diuretic, Antispasmodic, Uterine relaxant, Anti-obesity agent, Anorectic, Spasnolytics, Anabolic agent, Erythropoietic agent, Anti-asthmatic, Expectorant, Cough suppressant, Mucolytic, Anti-uricemic agent, Dental vehicle, Breath freshener, Antacid, Anti-diuretic, Anti-flatulent, Beta-blocker, Teeth Whitener, Enzyme, Co-enzyme, Protein, Energy booster, Fibre, Probiotics, Prebiotics, NSAID, Anti-tussives, Decongestants, Anti-histamines, Expectorants, Anti-diarrhoeals, Hydrogen antagonists, Proton pump inhibitors, General nonselective CNS depressants, General nonselective CNS stimulants, Selectively CNS function modifying drugs, Antiparkinsonism, Narcotic-analgetics, Analgetic-antipyretics, Psychopharmacological drugs, and Sexual dysfunction agents.

Examples of useful pharmaceutically active agents or pharmaceutically inactive precursors thereof may also include: Casein glyco-macro-peptide (CGMP), Triclosan, Cetyl pyridinium chloride, Domiphen bromide, Quaternary ammonium salts, zinc components, Sanguinarine, Fluorides, Alexidine, Octonidine, EDTA, Aspirin, Acetaminophen, Ibuprofen, Ketoprofen, Diflunisal, Fenoprofen calcium, Naproxen, Tolmetin sodium, Indomethacin, Benzonatate, Caramiphen edisylate, Menthol, Dextromethorphan hydrobromide, Theobromine hydrochloride, Chlophendianol Hydrochloride, Pseudoephedrine Hydrochloride, Phenylephrine, Phenylpropanolamine, Pseudoephedrine sulphate, Brompheniramine maleate, Chlorpheniramine-maleate, Carbinoxamine maleate, Clemastine fumarate, Dexchlorpheniramine maleate, Dephenhydramine hydrochloride, Diphenpyralide hydrochloride, Azatadine maleate, Diphenhydramine citrate, Doxylamine succinate, Promethazine hydrochloride, Pyrilamine maleate, Tripellenamine citrate, Triprolidine hydrochloride, Acrivastine, Loratadine, Brompheniramine, Dexbrompheniamine, Guaifenesin, Ipecac, potassium iodide, Terpin hydrate, Loperamide, Famotidine, Ranitidine, Omeprazole, Lansoprazole, Aliphatic alcohols, Barbiturates, caffeine, strychnine, Picrotoxin, Pentyenetetrazol, Phenyhydantoin, Phenobarbital, Primidone, Carbamazapine, Etoxsuximide, Methsuximide, Phensuximide, Trimethadione, Diazepam, Benzodiazepines, Phenacemide, Pheneturide, Acetazolamide, Sulthiame, bromide, Levodopa, Amantadine, Morphine, Heroin, Hydromorphone, Metopon, Oxymorphone, Levophanol, Codeine, Hydrocodone, Xycodone, Nalorphine, Naloxone, Naltrexone, Salicylates, Phenylbutazone, Indomethacin, Phenacetin, Chlorpromazine, Methotrimeprazine, Haloperidol, Clozapine, Reserpine, Imipramine, Tranylcypromine, Phenelzine, Lithium, Sildenafil citrate, Tadalafil, and Vardenafil CL. For example, eugenol can be used as anaesthetic.

Examples of useful pharmaceutically active agent or pharmaceutically inactive precursor thereof may include active ingredients selected from the groups of ace-inhibitors, antianginal drugs, anti-arrhythmias, anti-asthmatics, anti-cholesterolemics, analgesics, anaesthetics, anticonvulsants, anti-depressants, anti-diabetic agents, anti-diarrhoea preparations, antidotes, anti-histamines, anti-hypertensive drugs, anti-inflammatory agents, anti-lipid agents, anti-manics, anti-nauseants, anti-stroke agents, anti-thyroid preparations, anti-tumour drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplasties, antiparkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra™, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocriptine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumour drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of useful pharmaceutically active agents or pharmaceutically inactive precursors thereof contemplated can also include antacids, H2-antagonists, and analgesics. For example, antacid dosages can be prepared using the ingredients calcium carbonate alone or in combination with magnesium hydroxide, and/or aluminium hydroxide. Moreover, antacids can be used in combination with H2-antagonists.

Analgesics include opiates and opiate derivatives, such as Oxycontin™, ibuprofen, aspirin, acetaminophen, and combinations thereof that may optionally include caffeine.

Other useful pharmaceutically active agents or pharmaceutically inactive precursors thereof can include anti-diarrhoeals such as Immodium™ AD, anti-histamines, anti-tussives, decongestants, vitamins, and breath fresheners. Also contemplated for use herein are anxiolytics such as Xanax™; anti-psychotics such as Clozaril™ and Haldol™; non-steroidal anti-inflammatories (NSAID's) such as ibuprofen, naproxen sodium, Voltaren™ and Lodine™, anti-histamines such as Claritin™, Hismanal™, Relafen™, and Tavist™; antiemetics such as Kytril™ and Cesamet™; bronchodilators such as Bentolin™, Proventil™; anti-depressants such as Prozac™, Zoloft™, and Paxil™; anti-migraines such as Imigra™, ACE-inhibitors such as Vasotec™, Capoten™ and Zestril™; anti-Alzheimer's agents, such as Nicergoline™; and CaH-antagonists such as Procardia™, Adalat™, and Calan™.

The popular H2-antagonists which are contemplated for use in the present invention include cimetidine, ranitidine hydrochloride, famotidine, nizatidine, ebrotidine, mifentidine, roxatidine, pisatidine and aceroxatidine.

Active antacid ingredients can include, but are not limited to, the following: aluminium hydroxide, dihydroxyaluminium aminoacetate, aminoacetic acid, aluminium phosphate, dihydroxyaluminium sodium carbonate, bicarbonate, bismuth aluminate, bismuth carbonate, bismuth subcarbonate, bismuth subgallate, bismuth subnitrate, bismuth subsilysilate, calcium phosphate, citrate ion (acid or salt), amino acetic acid, hydrate magnesium aluminate sulphate, magaldrate, magnesium aluminosilicate, magnesium carbonate, magnesium glycinate, magnesium hydroxide, magnesium oxide, magnesium trisilicate, milk solids, aluminium mono-ordibasic calcium phosphate, tricalcium phosphate, potassium bicarbonate, sodium tartrate, sodium bicarbonate, magnesium aluminosilicates, tartaric acids and salts.

In some embodiments, the pharmaceutically active agent or pharmaceutically inactive precursor thereof can be selected from analgesics/anaesthetics such as menthol, phenol, hexylresorcinol, benzocaine, dyclonine hydrochloride, benzyl alcohol, salicyl alcohol, and combinations thereof. In some embodiments, the pharmaceutically active agent or pharmaceutically inactive precursor thereof can be selected from demulcents such as slippery elm bark, pectin, gelatin, and combinations thereof. In some embodiments, the pharmaceutically active agent or pharmaceutically inactive precursor thereof can be selected from antiseptic ingredients such as cetylpyridinium chloride, domiphen bromide, dequalinium chloride, eugenol and combinations thereof.

In some embodiments, the pharmaceutically active agent or pharmaceutically inactive precursor thereof can be selected from antitussive ingredients such as chlophedianol hydrochloride, codeine, codeine phosphate, codeine sulphate, dextromethorphan, dextromethorphan hydrobromide, diphenhydramine citrate, and diphenhydramine hydrochloride, and combinations thereof.

In some embodiments, the pharmaceutically active agent or pharmaceutically inactive precursor thereof can be selected from throat soothing agents such as honey, propolis, aloe vera, glycerine, menthol and combinations thereof. In still other embodiments, the pharmaceutically active agent or pharmaceutically inactive precursor thereof can be selected from cough suppressants. Such cough suppressants can fall into two groups: those that alter the texture or production of phlegm such as mucolytics and expectorants; and those that suppress the coughing reflex such as codeine (narcotic cough suppressants), antihistamines, dextromethorphan and isoproterenol (non-narcotic cough suppressants).

In still other embodiments, the pharmaceutically active agent or pharmaceutically inactive precursor thereof can be an antitussive selected from the group comprising codeine, dextromethorphan, dextrorphan, diphenhydramine, hydrocodone, noscapine, oxycodone, pentoxyverine and combinations thereof. In some embodiments, the pharmaceutically active agent or pharmaceutically inactive precursor thereof can be selected from antihistamines such as acrivastine, azatadine, brompheniramine, chlo[phi]heniramine, clemastine, cyproheptadine, dexbrompheniramine, dimenhydrinate, diphenhydramine, doxylamine, hydroxyzine, meclizine, phenindamine, phenyltoloxamine, promethazine, pyrilamine, tripelennamine, triprolidine and combinations thereof. In some embodiments, the pharmaceutically active agent or pharmaceutically inactive precursor thereof can be selected from non-sedating antihistamines such as astemizole, cetirizine, ebastine, fexofenadine, loratidine, terfenadine, and combinations thereof.

For example, the at least one active ingredient and/or inactive precursor thereof is selected from fragrances, flavours, essential oils, insecticide, fungicide, pharmaceutically active agent, or pharmaceutically inactive precursor thereof, e.g. antiseptic and/or anaesthetic, and mixtures thereof. Most preferably, the at least one active ingredient and/or inactive precursor thereof is a pharmaceutically active agent, or pharmaceutically inactive precursor thereof, e.g. antiseptic and/or anaesthetic, or a mixture thereof.

It is preferred that the at least one active ingredient and/or inactive precursor thereof is in liquid form.

The term "liquid" in the meaning of the present invention refers to a non-gaseous fluid composition, comprising or consisting of the at least one active ingredient and/or inactive precursor thereof, which is readily flowable at the pressure conditions and temperature of use, i.e. the temperature at which the method, preferably method step e2), is carried out.

It is appreciated that the at least one active ingredient and/or inactive precursor thereof can be used as such provided that it is in liquid form or in a solvent. If the at least one active ingredient and/or inactive precursor thereof is solid at room temperature, the at least one active ingredient and/or inactive precursor thereof is preferably provided in a (aqueous or organic) solvent such as to form a solution, a dispersion, e.g. a nano-dispersion, an emulsion, e.g. a nano-emulsion, or suspension, e.g. a nano-suspension.

If the at least one active ingredient and/or inactive precursor thereof is provided in a solvent, the solvent is preferably selected from the group comprising water, methanol, ethanol, n-butanol, isopropanol, n-propanol, n-octanol, acetone, dimethylsulphoxide, dimethylformamide, tetrahydrofurane, vegetable oils and the derivatives thereof, animal oils and the derivatives thereof, molten fats and waxes, and mixtures thereof, and more preferably the solvent is water, ethanol and/or acetone. More preferably, the solvent is ethanol and/or acetone.

If the at least one active ingredient and/or inactive precursor thereof is solid at room temperature, the at least one active ingredient and/or inactive precursor thereof can be also provided in a melted state, i.e. the at least one active ingredient and/or inactive precursor thereof is preferably provided in a melted state if the melting temperature is below 180° C., preferably from 20 to 100° C.

If the at least one active ingredient and/or inactive precursor thereof is liquid as such, the at least one active ingredient and/or inactive precursor thereof is preferably liquid in a temperature range from above 0° C., such as in a range from 3 to 180° C., preferably from 10 to 100° C. and most preferably from 10 to 40° C. For example, the at least one active ingredient and/or inactive precursor thereof is liquid in a temperature range from above 0° C., such as in a range from 3 to 180° C., preferably from 10 to 100° C. and most preferably from 10 to 40° C., at ambient pressure conditions, i.e. at atmospheric pressure.

In one embodiment, the at least one active ingredient and/or inactive precursor thereof is dissolved in a solvent. That is to say, the at least one active ingredient and/or inactive precursor thereof and the solvent form a system in which no discrete solid particles are observed in the solvent and thus form a "solution".

The term "suspension" refers to a system comprising essentially insoluble solids and solvent and optionally further additives and usually contains large amounts of solids and, thus, is more viscous and generally of higher density than the solvent from which it is formed. However, the term "essentially insoluble" does not exclude that at least a part of the solids material dissolves in water under certain conditions, e.g. at increased temperature.

If the at least one active ingredient and/or inactive precursor thereof is provided in a solvent, the solvent is preferably removed directly after method step e2), e.g. by evaporation. The term "directly after" means that no further step is implemented between loading step e2) and the defined removing of the solvent. However, it is appreciated that the removal of the solvent can be timely separated from method step e2).

In step e2) of the method of the present invention, the compacted form of the surface-reacted calcium carbonate obtained in step b) or the granules obtained in step c) or, if present, step d) is/are loaded with the at least one active ingredient and/or inactive precursor thereof. For example, the granules obtained in step d) are loaded with the at least one active ingredient and/or inactive precursor thereof.

Preferably, loading step e2) is carried out by spraying or dropping the at least one active ingredient and/or inactive precursor thereof onto the compacted form of the surface-reacted calcium carbonate obtained in step b) or the granules obtained in step c) or, if present, step d) and mixing in a device which is suitable for evenly distributing the at least one active ingredient and/or inactive precursor thereof onto the compacted form of the surface-reacted calcium carbonate or the granules.

For the purposes of the present invention, any suitable means known in the art may be used. However, loading step e2) preferably takes place in a device selected from the group comprising fluidized bed dryers/granulators, ploughshare mixer, vertical or horizontal mixers, high or low shear mixer and high speed blenders.

It is appreciated that loading step e2) can be carried out over a broad temperature and/or pressure range. For example, loading step e2) is carried out in a temperature range from above 0° C., such as in a range from 3 to 180° C., preferably from 10 to 100° C. and most preferably from 10 to 40° C., at ambient pressure conditions, i.e. at atmospheric pressure. Alternatively, loading step e2) is carried out in a temperature range from above 0° C., such as in a range from 3 to 180° C., preferably from 10 to 100° C. and most preferably from 10 to 40° C. under vacuum.

In one embodiment, loading step e2) is carried out at ambient temperature and pressure conditions, e.g., at room temperature, such as from about 5 to 35° C., preferably from 10 to 30° C. and most preferably from 15 to 25° C., and at atmospheric pressure. Alternatively, loading step e2) is carried out at ambient temperature, e.g., at room temperature, such as from about 5 to 35° C., preferably from 10 to 30° C. and most preferably from 15 to 25° C., and under vacuum.

If the method comprises the provision of at least one active ingredient and/or inactive precursor thereof, the method for producing a dosage form comprises, preferably consists of, the steps of:
 a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
 b) compacting the surface-reacted calcium carbonate of step a) by means of a roller compacter at a compaction pressure in the range from 1 to 30 kN/cm into a compacted form;
 c) milling the compacted form of step b) into granules; and
 e2) loading the compacted form obtained in step b) or the granules obtained in step c), preferably the granules obtained in step c), with at least one active ingredient and/or inactive precursor thereof for obtaining loaded granules;
 wherein the compacted form obtained in step b) consists of the surface-reacted calcium carbonate of step a).

In one embodiment, the method comprises a step of sieving the granules obtained in step c) such as to obtain granules of a specific grain size.

If the method further comprises a sieving, the method for producing a dosage form comprises, preferably consists of, the steps of:
 a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
 b) compacting the surface-reacted calcium carbonate of step a) by means of a roller compacter at a compaction pressure in the range from 1 to 30 kN/cm into a compacted form;
 c) milling the compacted form of step b) into granules; and
 e2) loading the compacted form obtained in step b) or the granules obtained in step c), preferably the granules obtained in step c), with at least one active ingredient and/or inactive precursor thereof for obtaining loaded granules;
 d) sieving of the granules of step c) or e2) by at least one mesh size;
 wherein the compacted form obtained in step b) consists of the surface-reacted calcium carbonate of step a).

It is preferred that the loading step e2) is carried out after sieving step d). Thus, the method for producing a dosage form comprises, preferably consists of, the steps of:
 a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
 b) compacting the surface-reacted calcium carbonate of step a) by means of a roller compacter at a compaction pressure in the range from 1 to 30 kN/cm into a compacted form;
 c) milling the compacted form of step b) into granules;
 d) sieving of the granules of step c) by at least one mesh size; and
 e2) loading the granules obtained in step d) with at least one active ingredient and/or inactive precursor thereof for obtaining loaded granules;
 wherein the compacted form obtained in step b) consists of the surface-reacted calcium carbonate of step a).

In one embodiment, the method comprises the provision of at least one active ingredient and/or inactive precursor thereof and the provision of at least one formulating aid. Thus, the method for producing a dosage form comprises, preferably consists of, the steps of:
 a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
b) compacting the surface-reacted calcium carbonate of step a) by means of a roller compacter at a compaction pressure in the range from 1 to 30 kN/cm into a compacted form;
c) milling the compacted form of step b) into granules;
e1) mixing the granules obtained in step c) with at least one formulating aid; and
e2) loading the compacted form obtained in step b) or the granules obtained in step c), preferably the granules obtained in step c), with at least one active ingredient and/or inactive precursor thereof for obtaining loaded granules;
wherein the compacted form obtained in step b) consists of the surface-reacted calcium carbonate of step a).

If the method further comprises a sieving, the method for producing a dosage form comprises, preferably consists of, the steps of:
a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
b) compacting the surface-reacted calcium carbonate of step a) by means of a roller compacter at a compaction pressure in the range from 1 to 30 kN/cm into a compacted form;
c) milling the compacted form of step b) into granules;
d) sieving of the granules of step c) or e2) by at least one mesh size;
e1) mixing the granules obtained in step d) with at least one formulating aid; and
e2) loading the compacted form obtained in step b) or the granules obtained in step c) or step d), preferably the granules obtained in step d), with at least one active ingredient and/or inactive precursor thereof for obtaining loaded granules;
wherein the compacted form obtained in step b) consists of the surface-reacted calcium carbonate of step a).

Preferably, the loading step e2) is carried out after the sieving step d). In this embodiment, the method for producing a dosage form comprises, preferably consists of, the steps of:
a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
b) compacting the surface-reacted calcium carbonate of step a) by means of a roller compacter at a compaction pressure in the range from 1 to 30 kN/cm into a compacted form;
c) milling the compacted form of step b) into granules;
d) sieving of the granules of step c) by at least one mesh size;
e1) mixing the granules obtained in step d) with at least one formulating aid; and
e2) loading the granules obtained in step d) with at least one active ingredient and/or inactive precursor thereof for obtaining loaded granules;
wherein the compacted form obtained in step b) consists of the surface-reacted calcium carbonate of step a).

If the method comprises method step e1) and step e2), these steps can be carried out simultaneously or separately in any order.

In one embodiment, method step e1) and step e2) are carried out simultaneously. For example, method step e1) and step e2) are carried out simultaneously in that the at least one formulating aid and the at least one active ingredient and/or inactive precursor thereof are provided in a blend. That is to say, said at least one formulating aid and the at least one active ingredient and/or inactive precursor thereof may be pre-mixed prior method step e1) and step e2) are carried out.

In one embodiment, method step e1) and step e2) are carried out independently from each other, i.e. separately in any order. For example, method step e2) is carried out before step e1).

It is appreciated that the granules obtained in step e2) can be subjected to a coating step e3), i.e. before optional tableting step f) is carried out. Such coatings are well known in the art and can be prepared with any conventional coating means known to the skilled person. Preferably, the coating step is carried out with the at least one formulating aid defined for mixing step e1).

In a further optional embodiment, the method further comprises a final step f) of tableting the granules obtained in step e2) or step e1) or step d), provided that step d) is carried out after step e2) or step e1), or filling the granules obtained in step e2) or step e1) or step d), provided that step d) is carried out after step e2) or step e1), into capsules.

The term "tableting" in the meaning of the present invention refers to a process of compacting or moulding a material into the shape of a tablet. The tablet may be in any shape and size known in the art. The "capsules" may be any kind of capsule known in the art. For example, the capsules can be gelatine or HPMC capsules.

The step f) is carried out at a compressive force in the range from 0.5 to 100 kN. It is to be noted that the compressive force used in step f) depends on the specific at least one active ingredient and/or inactive precursor thereof provided in step e2). The skilled person will thus adapt the compressive force accordingly. Preferably, the step f) is carried out at a compressive force in the range from 1.0 to 100 kN, and most preferably in the range from 1.5 to 80 kN. For example, step f) is carried out at a compressive force in the range from 2.0 to 60 kN, and most preferably in the range from 2.5 to 50 kN or from 2.5 to 20 kN.

Tableting can be carried out with any conventional compactor known to the skilled person. For example, tableting is carried out with a tablet press such as a Fette 1200i tablet press from Fette Compacting GmbH, Germany.

It is appreciated that the tablets obtained in tableting step f) can be subjected to a final coating step. Such coatings are well known in the art and can be prepared with any conventional coating means known to the skilled person.

In this embodiment, the method for producing a dosage form comprises, preferably consists of, the steps of:
a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;

b) compacting the surface-reacted calcium carbonate of step a) by means of a roller compacter at a compaction pressure in the range from 1 to 30 kN/cm into a compacted form;
c) milling the compacted form of step b) into granules;
e1) optionally mixing the granules obtained in step e2) with at least one formulating aid;
e2) loading the compacted form obtained in step b) or the granules obtained in step c), preferably the granules obtained in step c), with at least one active ingredient and/or inactive precursor thereof for obtaining loaded granules; and
f) tableting the granules obtained in step e1) or filling the granules obtained in step e1) into capsules;
wherein the compacted form obtained in step b) consists of the surface-reacted calcium carbonate of step a).

If the method further comprises a sieving, the method for producing a dosage form comprises, preferably consists of, the steps of:
a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
b) compacting the surface-reacted calcium carbonate of step a) by means of a roller compacter at a compaction pressure in the range from 1 to 30 kN/cm into a compacted form;
c) milling the compacted form of step b) into granules;
d) sieving of the granules of step e2) or, if present, e1) by at least one mesh size;
e1) optionally mixing the granules obtained in step e2) with at least one formulating aid;
e2) loading the compacted form obtained in step b) or the granules obtained in step c), preferably the granules obtained in step c), with at least one active ingredient and/or inactive precursor thereof for obtaining loaded granules;
f) tableting the granules obtained in step d) or filling the granules obtained in step d) into capsules;
wherein the compacted form obtained in step b) consists of the surface-reacted calcium carbonate of step a).

Preferably, the loading step e2) is carried out after the sieving step d). In this embodiment, the method for producing a dosage form comprises, preferably consists of, the steps of:
a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
b) compacting the surface-reacted calcium carbonate of step a) by means of a roller compacter at a compaction pressure in the range from 1 to 30 kN/cm into a compacted form;
c) milling the compacted form of step b) into granules;
d) sieving of the granules of step c) by at least one mesh size;
e1) optionally mixing the granules obtained in step e2) with at least one formulating aid;
e2) loading the granules obtained in step d) with at least one active ingredient and/or inactive precursor thereof for obtaining loaded granules; and
f) tableting the granules obtained in step e2) or, if present, step e1) or filling the granules obtained in step e2) or, if present, step e1) into capsules;
wherein the compacted form obtained in step b) consists of the surface-reacted calcium carbonate of step a).

Preferably, the method for producing a dosage form comprises, preferably consists of, the steps of:
a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
b) compacting the surface-reacted calcium carbonate of step a) by means of a roller compacter at a compaction pressure in the range from 1 to 30 kN/cm into a compacted form;
c) milling the compacted form of step b) into granules;
d) sieving of the granules of step c) by at least one mesh size;
e1) mixing the granules obtained in step e2) with at least one formulating aid;
e2) loading the granules obtained in step d) with at least one active ingredient and/or inactive precursor thereof for obtaining loaded granules; and
f) tableting the granules obtained in step e1) or filling the granules obtained in step e1) into capsules;
wherein the compacted form obtained in step b) consists of the surface-reacted calcium carbonate of step a).

Alternatively, the method for producing a dosage form comprises, preferably consists of, the steps of:
a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
b) compacting the surface-reacted calcium carbonate of step a) by means of a roller compacter at a compaction pressure in the range from 1 to 30 kN/cm into a compacted form;
c) milling the compacted form of step b) into granules;
d) sieving of the granules of step c) by at least one mesh size;
e1) mixing the granules obtained in step d) with at least one formulating aid;
e2) loading the granules obtained in step e1) with at least one active ingredient and/or inactive precursor thereof for obtaining loaded granules; and
f) tableting the granules obtained in step e2) or filling the granules obtained in step e2) into capsules;
wherein the compacted form obtained in step b) consists of the surface-reacted calcium carbonate of step a).

In one embodiment, the method for producing a dosage form comprises, preferably consists of, the steps of:
a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;

b) compacting the surface-reacted calcium carbonate of step a) by means of a roller compacter at a compaction pressure in the range from 1 to 30 kN/cm into a compacted form;
c) milling the compacted form of step b) into granules;
d) sieving of the granules of step c) by at least one mesh size;
e1) mixing the granules obtained in step d) with at least one formulating aid;
e2) loading the granules obtained in step e1) with at least one active ingredient and/or inactive precursor thereof for obtaining loaded granules;
e3) coating the granules obtained in step e2) with at least one formulating aid;
f) tableting the granules obtained in step e3) or filling the granules obtained in step e3) into capsules; and
wherein the compacted form obtained in step b) consists of the surface-reacted calcium carbonate of step a).

Alternatively, the method for producing a dosage form comprises, preferably consists of, the steps of:
a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
b) compacting the surface-reacted calcium carbonate of step a) by means of a roller compacter at a compaction pressure in the range from 1 to 30 kN/cm into a compacted form;
c) milling the compacted form of step b) into granules;
d) sieving of the granules of step c) by at least one mesh size;
e1) mixing the granules obtained in step e2) with at least one formulating aid;
e2) loading the granules obtained in step d) with at least one active ingredient and/or inactive precursor thereof for obtaining loaded granules;
e3) coating the granules obtained in step e1) with at least one formulating aid; and
f) tableting the granules obtained in step e3) or filling the granules obtained in step e3) into capsules;
wherein the compacted form obtained in step b) consists of the surface-reacted calcium carbonate of step a).

The dosage form obtained by the method may be a granule, tablet, mini-tablet or capsule.

Thus, in one aspect, the present invention further refers to granules consisting of the surface reacted calcium carbonate as defined herein and optionally mixed with at least one formulating aid as defined herein and/or loaded with at least one active ingredient and/or inactive precursor thereof as defined herein. For example, the granules consist of the surface reacted calcium carbonate as defined herein and mixed and/or coated with at least one formulating aid as defined herein and/or loaded with at least one active ingredient and/or inactive precursor thereof as defined herein. Preferably, the granules consist of the surface reacted calcium carbonate as defined herein and mixed with at least one formulating aid as defined herein or loaded with at least one active ingredient and/or inactive precursor thereof as defined herein, preferably loaded with at least one active ingredient and/or inactive precursor thereof as defined herein. Alternatively, the granules consist of the surface reacted calcium carbonate as defined herein and mixed with at least one formulating aid as defined herein and loaded with at least one active ingredient and/or inactive precursor thereof as defined herein. Preferably, the granules are obtained by the method as defined herein.

In another aspect, the present invention further refers to tablets and/or capsules obtained by the method as defined herein.

The dosage form thus may be prepared in a wide size range, wherein different size fractions may be separated by conventional means such as sieving.

Generally, the dosage form may have a weight median particle size of from 0.1 to 20.0 mm, preferably 0.2 to 15.0 mm and more preferably from 0.3 to 10.0 mm.

In view of the good results obtained the present invention refers in another aspect to the dosage form, preferably a tablet, mini-tablet or capsule, obtained by the method.

Another aspect refers to the use of the granules as defined herein, or the tablets and/or capsules as defined herein, or the dosage form as defined herein in a pharmaceutical, nutraceutical, agricultural, cosmetic, home, packaging food, and personal care product.

According to a further aspect, a pharmaceutical, nutraceutical, agricultural, cosmetic, home, food, packaging and personal care product comprising the granules as defined herein, or the tablets and/or capsules as defined herein, or the dosage form as defined herein, is provided.

A further aspect refers to the use of a surface-reacted calcium carbonate in a method as defined herein.

With regard to the definition of the method, the dosage form, the surface-reacted calcium carbonate, the at least one active ingredient and/or inactive precursor thereof, the at least one formulating aid and preferred embodiments thereof, reference is made to the statements provided above when discussing the technical details of the method of the present invention.

Figure 1:
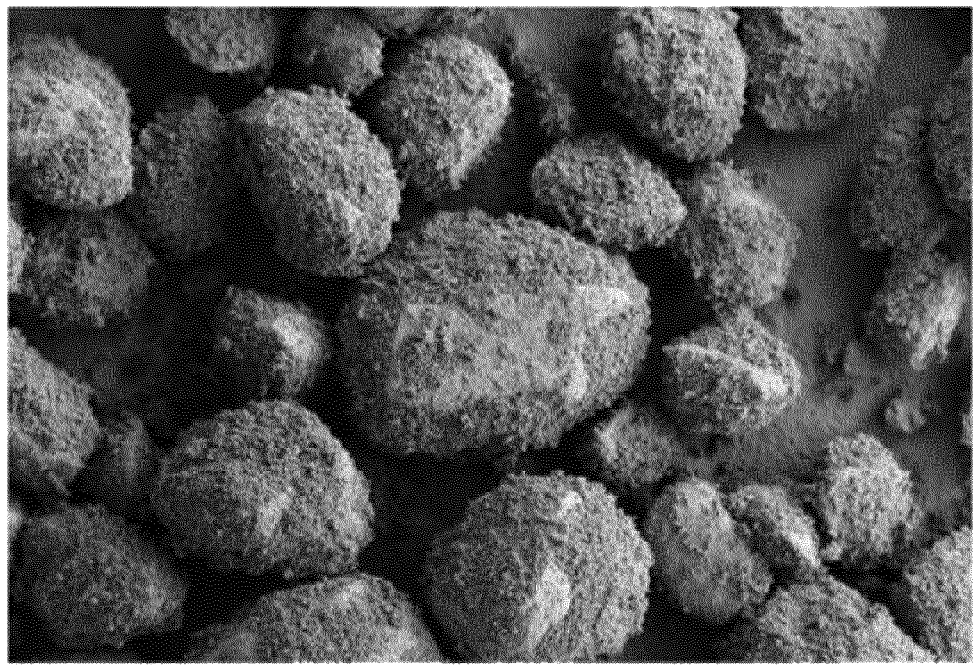
FIG. 1 shows a SEM picture of FCC consisting granules.

The following examples and tests will illustrate the present invention, but are not intended to limit the invention in any way.

EXAMPLES

Materials and Methods
1. Measurement Methods
The following measurement methods were used to evaluate the parameters given in the examples and claims.
BET Specific Surface Area (SSA) of a Material
The BET specific surface area was measured via the BET process according to ISO 9277 using nitrogen, following conditioning of the sample by heating at 250° C. for a period of 30 minutes. Prior to such measurements, the sample was filtered, rinsed and dried at 110° C. in an oven for at least 12 hours.

Particle Size Distribution (Volume % Particles with a Diameter <X), $d_{50}$ Value (Volume Median Grain Diameter) and $d_{98}$ Value of a Particulate Material:

Volume median grain diameter $d_{50}$ was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement is analysed using the Mie theory, with a particle refractive index of 1.57 and an absorption index of 0.005.

The weight median grain diameter is determined by the sedimentation method, which is an analysis of sedimentation behaviour in a gravimetric field. The measurement is made with a Sedigraph™ 5100 of Micromeritics Instrument Corporation. The method and the instrument are known to the skilled person and are commonly used to determine grain size of fillers and pigments. The measurement is carried out in an aqueous solution of 0.1 wt.-% $Na_4P_2O_7$. The samples were dispersed using a high speed stirrer and sonicated.

A vibrating sieve tower was used to analyze the particle size distribution of the granules. Aliquots of 120 g of granules were put on steel wire screens (Retsch, Germany) with mesh sizes of 90 μm, 180 μm, 250 μm, 355 μm, 500 μm, 710 μm and 1 mm. The sieving tower was shaken for 3 minutes with 10 seconds interval at a shaking displacement of 1 mm.

The processes and instruments are known to the skilled person and are commonly used to determine grain size of fillers and pigments.

Intra-Particle Intruded Specific Pore Volume (in $Cm^3/g$) of Surface Reacted Calcium Carbonate The specific pore volume is measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 μm (~nm). The equilibration time used at each pressure step is 20 seconds. The sample material is sealed in a 5 $cm^3$ chamber powder penetrometer for analysis. The data are corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p 1753-1764.).

The total pore volume seen in the cumulative intrusion data can be separated into two regions with the intrusion data from 214 μm down to about 1-4 μm showing the coarse packing of the sample between any agglomerate structures contributing strongly. Below these diameters lies the fine inter-particle packing of the particles themselves. If they also have intra-particle pores, then this region appears bi modal, and by taking the specific pore volume intruded by mercury into pores finer than the modal turning point, i.e. finer than the bi-modal point of inflection, we thus define the specific intra-particle pore volume. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the inter-particle pore region and the intra-particle pore region, if present. Knowing the intra-particle pore diameter range it is possible to subtract the remainder inter-particle and inter-agglomerate pore volume from the total pore volume to deliver the desired pore volume of the internal pores alone in terms of the pore volume per unit mass (specific pore volume). The same principle of subtraction, of course, applies for isolating any of the other pore size regions of interest.

Intra-Particle Intruded Specific Pore Volume (in $Cm^3/g$) of Surface Reacted Calcium Carbonate Granules Loaded with Active The specific pore volume is measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 μm (~nm). The equilibration time used at each pressure step is 20 seconds. The sample material is sealed in a 3 cm3 chamber powder penetrometer for analysis. The data are corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p 1753-1764).

The first derivative of the cumulative intrusion curve showed the intra and inter-particle pore volume regions are not independent and separable in all cases. Thus, in order to show the pore volume difference for the loaded samples compared to the empty granules, the pore volume for each sample was obtained by taking the cumulative intrusion curve for pore diameters below 5 μm, representing the intrusion volume from the sum of the intra and inter particle pore volumes of the granulated materials.

Loose Bulk Density 120 g of the granules of selected granular fraction (from 180 μm to 710 μm) were sieved through a 0.5 mm screen by means of a brush. 100±0.5 g of this sample were carefully filled through a powder funnel into the 250 mL measuring cylinder and the volume was read off to the nearest 1 mL. The loose bulk density was the calculated according the formula:

Loose bulk density [g/mL]=bulk volume [mL]/weighed sample [g]

and the result was recorded to the nearest 0.01 g/mL.

Tapped Density 120 g of the granules of selected granular fraction (from 180 μm to 710 μm) were sieved through a 0.5 mm screen by means of a brush. 100±0.5 g of this sample were carefully filled through a powder funnel into the 250 mL measuring cylinder. The graduated cylinder is connected to a support provided with a settling apparatus capable of producing taps. The cylinder is secured in this support and the volume after 1250 taps is read. A subsequent second tapping step consisting of 1250 taps is performed and the value of the volume is read. When this second tapped volume value does not differ in more than 2 mL from this first tapped volume value, this is the tapped volume. When this value differs in more than 2 mL, the tapping step of 1250 taps is repeated until no differences of more than 2 mL in subsequent steps is observed.

Angle of Repose

Figure 7:
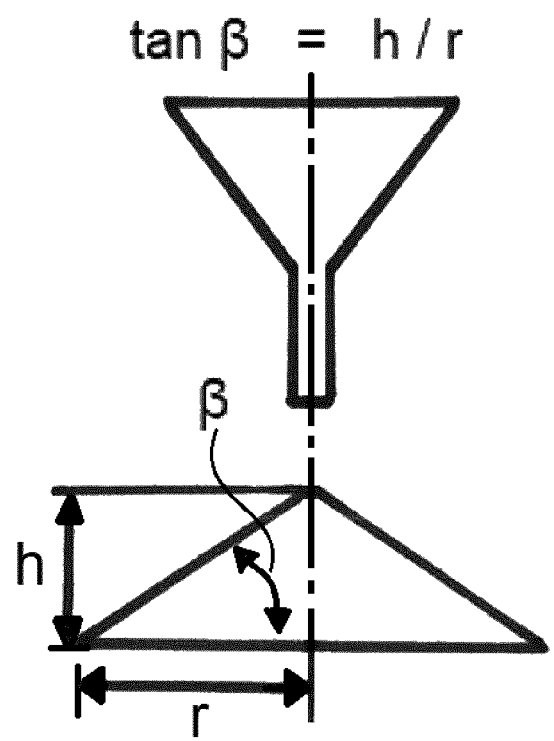
FIG. 7 depicts calculation of the angle of repose (β) in a flowability tester using the equation tan β=h/r.

The angle of repose is measured in a flowability tester. The hopper equipped with the 10 mm nozzle is filled with approximately 150 ml of granulate. After emptying the hopper, the granulate bevel is measured by means of a laser beam and the angle of repose is calculated. The angle of repose B is the angle of the bevel flank opposite the horizontal line that is calculated as shown in FIG. 7.

Compressibility Index

The compressibility index is calculated as follows:

Compressibility Index=(Tapped density−Bulk density)/Tapped density*100

Thermo Gravimetric Analysis (TGA)

The TGA is basically used to determine the loss ignition of mineral samples and filled organic materials. The equipment used to measure the TGA was the Mettler-Toledo TGA/DSC1 (TGA 1 STARe System) and the crucibles used were aluminium oxide 900 µl. The method consists of two heating steps the first between 30-130° C. for 10 minutes at a heating rate of 20° C./minute and the second one between 130-570° C. for 20 minutes at a heating rate of 20° C./minute.

2. Material

Surface-reacted calcium carbonate (FCC), (from Omya International AG, Switzerland) was compared to microcrystalline cellulose (Avicel® PH 102, FMC BioPolymer, Ireland). Further details of the surface-reacted calcium carbonate are summarized in the following table 1:

TABLE 1

| Apparent true density [g/cm$^3$] | Mean weight median particle size [µm] | Top cut particle size $d_{98}$ [µm] | BET Specific surface area [m$^2$/g] | Core voids [%, v/v] | Stratum/ and interparticle voids [%, v/v] | Intra-particle intruded specific pore volume [cm$^3$/g] |
|---|---|---|---|---|---|---|
| 2.7259 | 6.15 | 15 | 55.52 | 11 | 89 | 0.97 |

Eugenol (≥98%, FCC, FG, Sigma Aldrich, W246700, CAS No. 97-53-0,

EC No. 202-589-1) and ibuprofen (Shashun Pharmaceuticals Limited, BP/Ph.Eur., Cas #15687-27-1) were chosen as active ingredients.

3. Granulation Experiments

Granulation of FCC by Roller Compaction

The granulation was performed using the Fitzpatrick CCS220. A bar mill and a rasped 1 mm screen were used for granulation. The parameters set were:

| | |
|---|---|
| Roll gap | 0.7 mm (actual value during process 0.9 rpm) |
| Roll force | 5 kN/cm |
| Roll speed | 8 rpm |
| Horizontal screw speed | 25 rpm (actual value during process 13 rpm) |
| Vertical screw speed | 250 rpm |
| Mill speed | 500 rpm |

The granule fraction between 250-710 µm was produced using a Retsch tower sieve shaker AS300 with 90, 180, 250, 355, 500, 710 and 1000 µm.

The particle size distribution and further parameters are outlined in tables 2, 3 and 4.

TABLE 2

Particle size distribution of manufactured empty granules

| Mean PSD Granules manufactured with FCC (Mass fraction %) | Granule size range (µm) |
|---|---|
| 0.01 | 0-90 |
| 3.32 | 90-180 |
| 18.37 | 180-250 |
| 17.90 | 250-355 |
| 18.34 | 355-500 |
| 36.18 | 500-710 |
| 5.85 | 710-1 000 |
| 0.01 | <1 000 |

TABLE 3

Parameters measured in the 250-710 µm range

| Parameters | Empty granules |
|---|---|
| Specific surface area (m$^2$/g) | 52 |
| Particle median diameter (sieve) ($d_{50}$, µm) | 500 |
| Bulk density (g/mL) | 0.48 |
| Tapped density (g/mL) | 0.61 |
| Compressibility Index | 21.31 |
| Angle of repose (°) | 47 |

TABLE 4

Pore Volume

| Parameters | Empty granules |
|---|---|
| Truncated volume cm$^3$/g - diameter range 0.004-4.9 µm | 0.897 |

Tableting with Granules Obtained from FCC Granules Loaded with Eugenol

The granules obtained from eugenol loaded FCC were further mixed with 0.5 wt.-% lubricant (Magnesium stearate, Ligamed MF-2-V, Cas #557-04-0, Peter Greven) in a Turbula Mixer (Willy A. Bachofen, Turbula T10B) for 5 minutes. The mix was further used to prepare tablets in a Fette 1200i using EU1" tooling, a 10 mm fill cam, 8 standard convex round 10 mm punches and a tableting speed of 15000 tablets/hour. The fill depth was adjusted to obtain compression forces of 2, 4 and 6 kN and the table weight was fixed at 175 mg. The tableting parameters are outlined in table 5.

TABLE 5

Tableting parameters

| Parameters | | Tablet hardness empty granules (N) |
|---|---|---|
| Compression force (kN) | 2 | 35 |
| | 4 | 83 |
| | 6 | 119 |

A SEM picture of FCC consisting granules is shown in FIG. 1.

Loading FCC Granules with Eugenol 150 g of FCC granules (250-710 µm) were placed on a 3 L plastic beaker. The granules were loaded with 16.7 g (10 wt.-%), 50 g (25 wt.-%) and 100 g of eugenol (40 wt.-%) of Eugenol (Sigma Aldrich W246700). The eugenol was loaded by dropping at a rate of 1-2 drops/second by means of a peristaltic pump Ismatec IPC 8 with a two-stop tubing 1.52 mm wide. While loading, the granules were permanently mixed with an overhead stirrer IKA RW20 at a speed ranging between 80 and 120 rpm using an open blade paddle mixer. After the total amount of liquid was loaded onto the FCC granules the loaded granules were left to mix 10 minutes longer.

The results obtained from eugenol loaded FCC granules are outlined in tables 6, 7 and 8.

TABLE 6

Particle size distribution of manufactured granules

| FCC granules loaded with 10 wt.-% eugenol. Mass fraction (%) | FCC granules loaded with 25 wt.-% eugenol Mass fraction (%) | FCC granules loaded with 40 wt.-% eugenol Mass fraction (%) | Granule size range (μm) |
|---|---|---|---|
| 0.13 | 1.06 | 0.13 | 0-90 |
| 3.56 | 4.18 | 1.82 | 90-180 |
| 7.49 | 5.31 | 3.47 | 180-250 |
| 14.41 | 11.41 | 9.11 | 250-355 |
| 26.35 | 25.40 | 21.30 | 355-500 |
| 47.43 | 50.27 | 44.52 | 500-710 |
| 0.57 | 1.86 | 14.23 | 710-1 000 |
| 0.06 | 0.53 | 5.42 | >1 000 |

TABLE 7

Parameters measured in the 250-710 μm range

| Parameters | FCC granules loaded with 10 wt.-% eugenol | FCC granules loaded with 25 wt.-% eugenol | FCC granules loaded with 40 wt.-% eugenol |
|---|---|---|---|
| Particle median diameter (sieve) ($d_{50}$, μm) | 499 | 510 | 568 |
| Bulk density (g/mL) | 0.56 | 0.69 | 1.1 |
| Tapped density (g/mL) | 0.67 | 0.76 | 0.93 |
| Compressibility Index | 16.42 | 9.21 | 15.45 |
| Angle of repose (°) | 50 | 45 | 64 |
| Loading % (TGA) | 8.21 | 23.80 | 39.53 |

TABLE 8

Pore Volume

| Parameters | Tablet hardness FCC granules loaded with 10 wt.-% eugenol. (N) | Tablet hardness granules manufactured with 25 wt.-% eugenol loaded FCC (N) | Tablet hardness granules manufactured with 40 wt.-% eugenol loaded FCC (N) |
|---|---|---|---|
| Truncated volume cm³/g - diameter range 0.004-4.9 μm | 0.701 | 0.409 | 0.105 |

Tableting with Granules Obtained from FCC Granules Loaded with Eugenol

The granules obtained from eugenol loaded FCC were further mixed with 0.5 wt.-% lubricant (Magnesium stearate, Ligamed MF-2-V, Cas #557-04-0, Peter Greven) in a Turbula Mixer (Willy A. Bachofen, Turbula T10B) for 5 minutes. The mix was further used to prepare tablets in a Fette 1200i using EU1" tooling, a 10 mm fill cam, 8 standard convex round 10 mm punches and a tableting speed of 15 000 tablets/hour. The fill depth was adjusted to obtain compression forces of 2, 4 and 6 kN and the table weight was fixed at 175 mg. The tableting parameters are outlined in table 9.

TABLE 9

Tableting parameters

| Parameters | | Tablet hardness FCC granules loaded with 10 wt.-% eugenol. (N) | Tablet hardness FCC granules loaded with 25 wt.-% eugenol. (N) | Tablet hardness FCC granules loaded with 40 wt.-% eugenol. (N) |
|---|---|---|---|---|
| Compression force (kN) | 2 | 33 | 20 | N/A |
| | 4 | 59 | 20 | N/A |
| | 6 | 85 | 16 | N/A |

Figure 2:
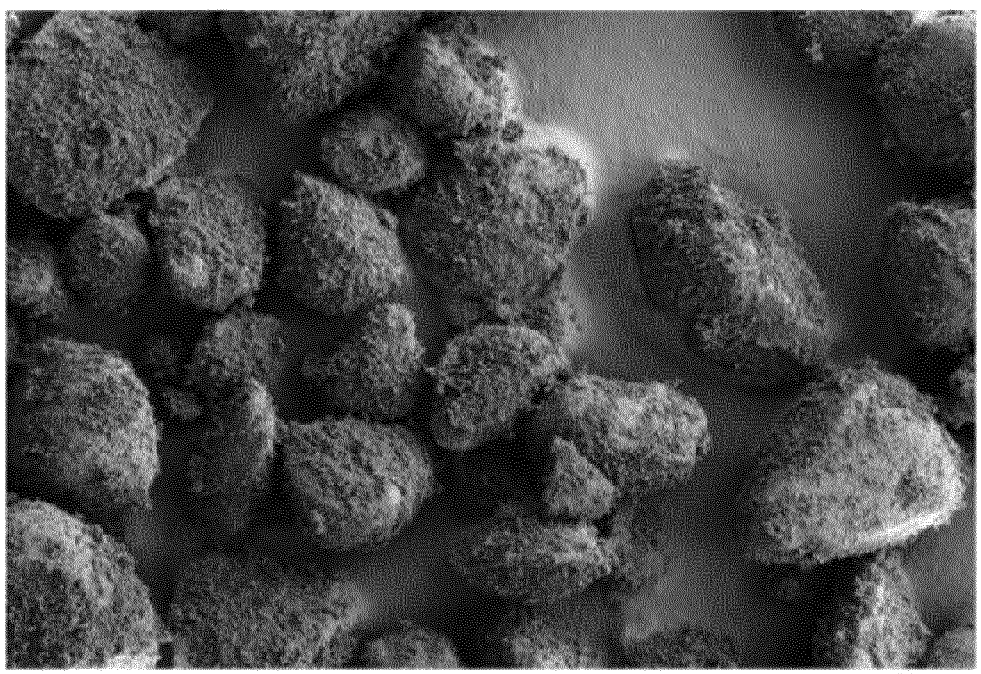
FIG. 2 shows a SEM picture of FCC consisting granules loaded with 10% eugenol.
Figure 3:
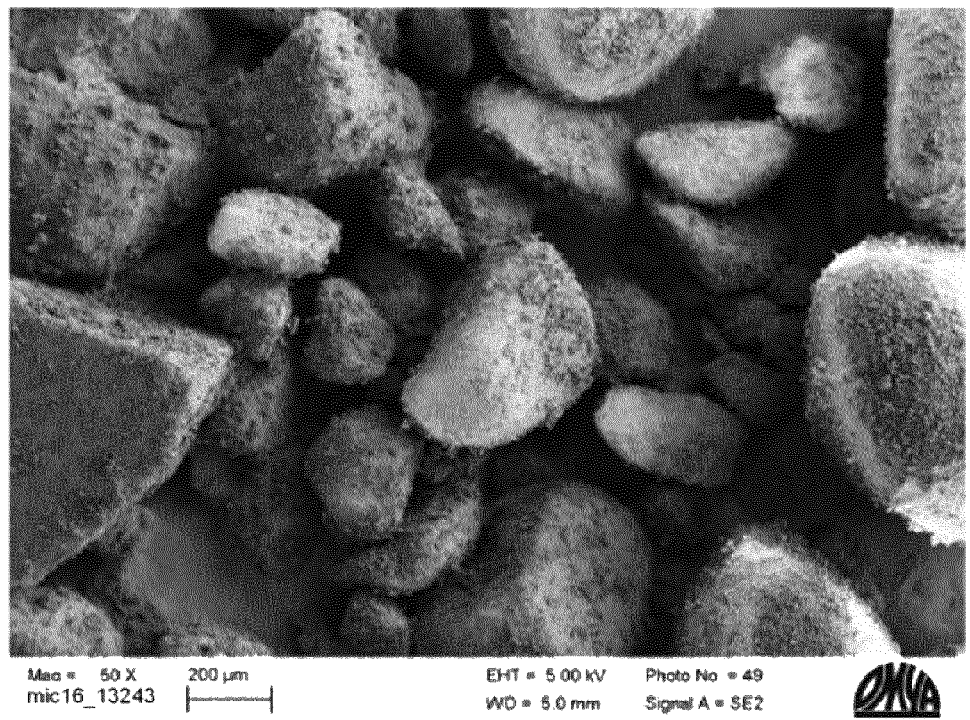
FIG. 3 shows a SEM picture of FCC consisting granules loaded with 25% eugenol.
Figure 4:
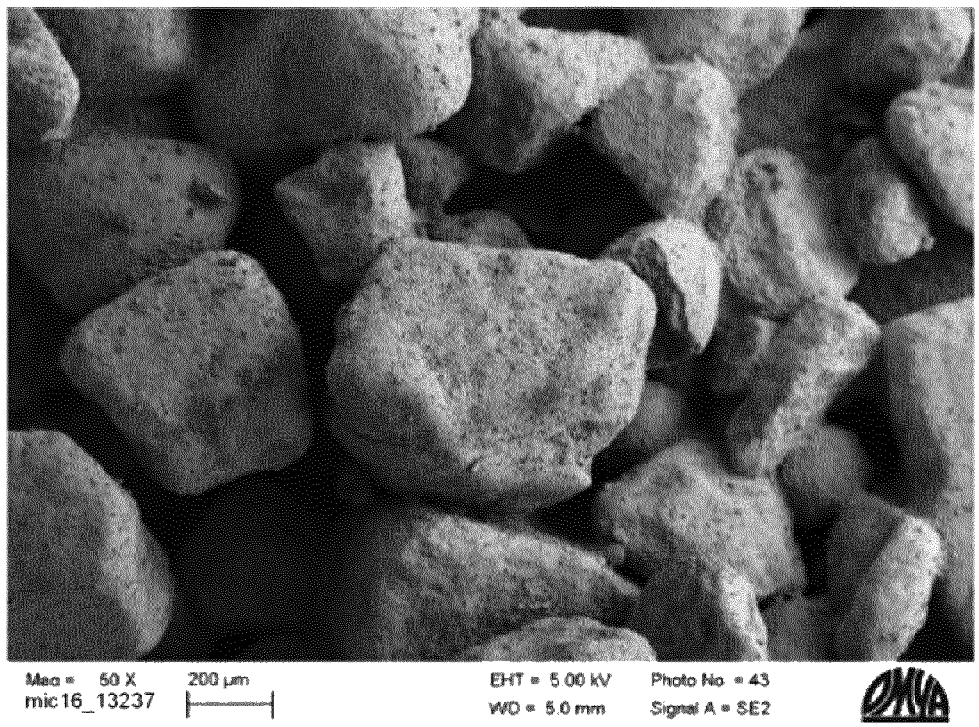
FIG. 4 shows a SEM picture of FCC consisting granules loaded with 40% eugenol.

SEM pictures of granules loaded with 10% or 25% or 40% eugenol are shown in FIGS. 2, 3 and 4.

Loading FCC Granules with Ibuprofen 150 g of FCC granules (250-710 μm) were placed on a 3 L plastic beaker. The powder was loaded with 16.7 g (10 wt.-%) and 100 g (40% w/w) of Ibuprofen (BASF). The ibuprofen was first dissolved in acetone 75 g and 150 g for the 10 wt.-% and 40 wt.-% loadings, respectively. The ibuprofen acetone solution was loaded by spraying at a rate of 5 hits every 15 seconds by means of a spray bottle. While loading, the granules were permanently mixed with an overhead stirrer IKA RW20 at a speed ranging between 80 and 120 rpm using an open blade paddle mixer. After the total amount of solution was loaded onto the FCC granules the loaded granules were left to mix 10 minutes longer. The loaded granules were dried at a vacuum oven ThermoScientific VT 6130 until no more solvent could be collected.

The results obtained from ibuprofen loaded FCC granules are outlined in tables 10, 11 and 12.

TABLE 10

Particle size distribution of manufactured granules

| FCC granules loaded with 10 wt.-% Ibuprofen | FCC granules loaded with 40 wt.-% Ibuprofen | Granule size range (μm) |
|---|---|---|
| 0.74 | 1.33 | 0-90 |
| 2.54 | 2.51 | 90-180 |
| 5.02 | 3.93 | 180-250 |
| 11.44 | 10.23 | 250-355 |
| 25.75 | 20.01 | 355-500 |
| 50.30 | 43.46 | 500-710 |
| 3.75 | 14.45 | 710-1 000 |
| 0.47 | 4.08 | >1 000 |

TABLE 11

Parameters measured in the 250-710 μm range

| Parameters | FCC granules loaded with 10 wt.-% Ibuprofen | FCC granules loaded with 40 wt.-% Ibuprofen |
|---|---|---|
| Particle median diameter (sieve) ($d_{50}$, μm) | 520 | 555 |
| Bulk density (g/mL) | 0.65 | 0.65 |
| Tapped density (g/mL) | 0.65 | 0.69 |
| Compressibility Index | 0 | 5.80 |
| Angle of repose (°) | 36.20 | 36.40 |
| Loading % (TGA) | 7.39 | 33.63 |

TABLE 12

Pore Volume

| Parameters | Tablet hardness FCC granules loaded with 10 wt.-% Ibuprofen (N) | Tablet hardness FCC granules loaded with 40 wt.-% Ibuprofen (N) |
|---|---|---|
| Truncated volume $cm^3/g$ - diameter range 0.004-4.9 μm | 0.629 | 0.420 |

Tableting with Granules Obtained from FCC Granules Loaded with Ibuprofen

The granules obtained from eugenol loaded FCC were further mixed with 0.5 wt.-% lubricant (Magnesium stearate, Ligamed MF-2-V, Cas #557-04-0, Peter Greven) in a Turbula Mixer (Willy A. Bachofen, Turbula T10B) for 5 minutes. The mix was further used to prepare tablets in a Fette 1200i using EU1" tooling, a 10 mm fill cam, 8 standard convex round 10 mm punches and a tableting speed of 15 000 tablets/hour. The fill depth was adjusted to obtain compression forces of 2, 4 and 6 kN and the table weight was fixed at 175 mg. The tableting parameters are outlined in table 13.

TABLE 13

Tableting parameters

| Parameters | | Tablet hardness FCC granules loaded with 10 wt.-% Ibuprofen (N) | Tablet hardness FCC granules loaded with 40 wt.-% Ibuprofen (N) |
|---|---|---|---|
| Compression force (kN) | 2 | 21 | 36 |
| | 4 | 45 | 67 |
| | 6 | 67 | 64 |

Figure 5:
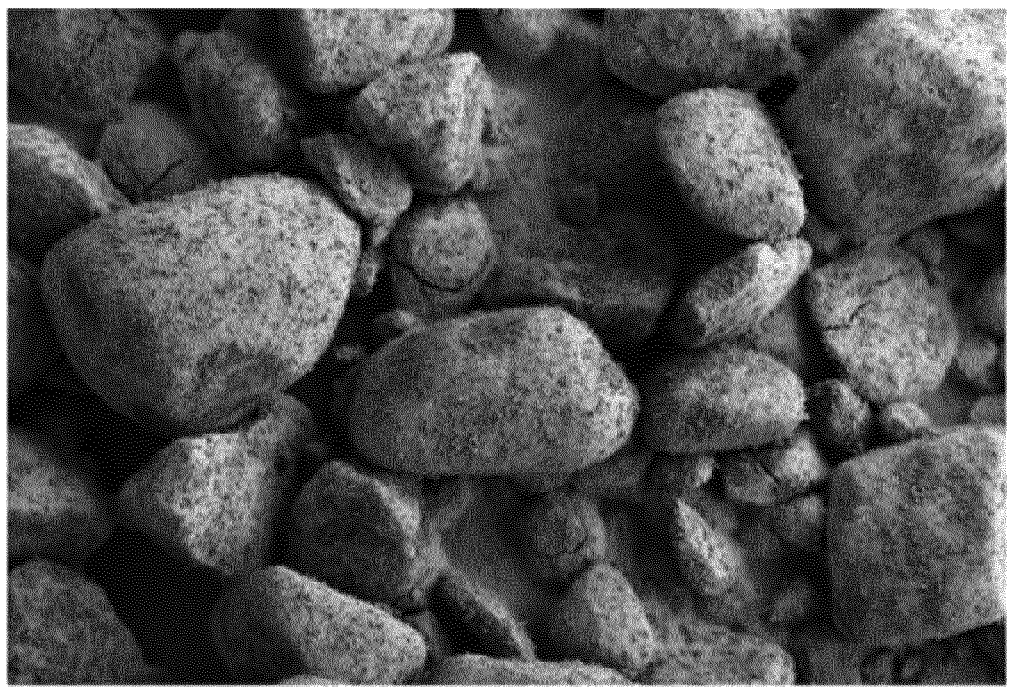
FIG. 5 shows a SEM picture of FCC consisting granules loaded with 10% ibuprofen.
Figure 6:
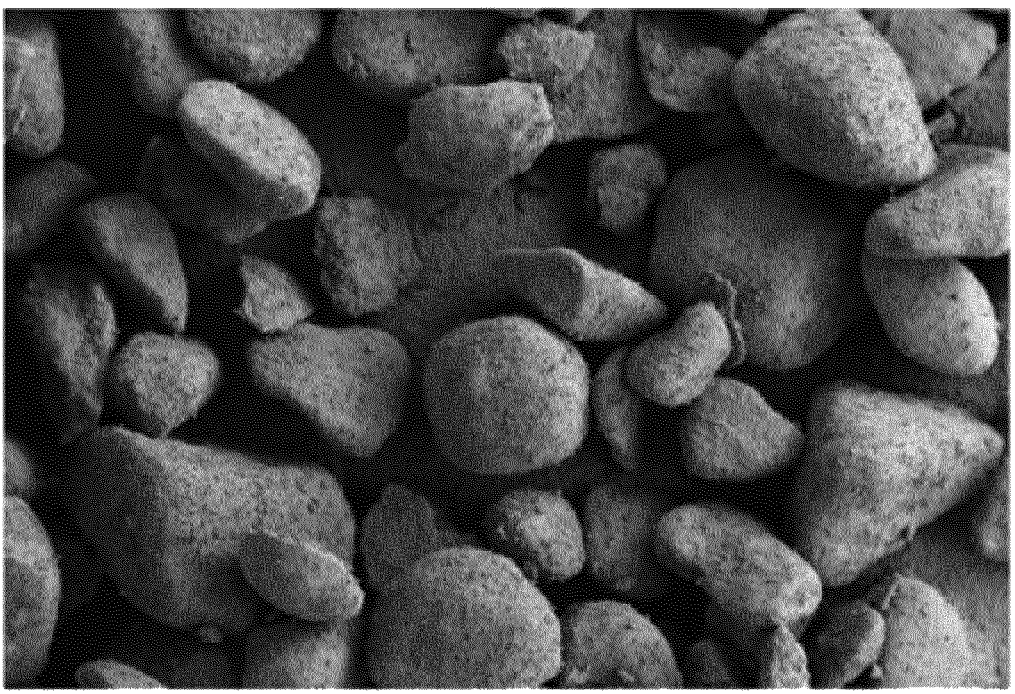
FIG. 6 shows a SEM picture of FCC consisting granules loaded with 40% ibuprofen.

SEM pictures of granules loaded with 10% or 40% ibuprofen are shown in FIGS. 5 and 6.

The invention claimed is:

1. A method of producing granules comprising surface-reacted calcium carbonate, the method comprising the steps of:
   a) providing the surface-reacted calcium carbonate, wherein the surface-reacted calcium carbonate is a reaction product of: (1) natural ground or precipitated calcium carbonate with (2) carbon dioxide and (3) one or more $H_3O^+$ ion donors in an aqueous medium, wherein the carbon dioxide is formed in-situ by the $H_3O^+$ ion donor treatment and/or is supplied from an external source;
   b) compacting the surface-reacted calcium carbonate of step a) by means of a roller compactor at a compaction pressure in the range from 1 kN/cm to 30 kN/cm into a compacted form;
   c) milling the compacted form of step b) into granules; and
   d) optionally, sieving the granules of step c) with at least one mesh size to obtain granules having a median grain size of from 180 μm to 710 μm;
   wherein the method further comprises loading the compacted form obtained in step b) or the granules obtained in step c) with at least one active ingredient and/or inactive precursor thereof, to obtain loaded granules, wherein the loading is carried out by spraying or dropping the at least one active ingredient and/or inactive precursor thereof onto the compacted form obtained in step b) or the granules obtained in step c), and mixing in a device selected from the group consisting of a fluidized bed dryer/granulator, a ploughshare mixer, a vertical mixer, a horizontal mixer, a high shear mixer, a low shear mixer and a high speed blender, wherein the at least one active ingredient and/or inactive precursor thereof is in liquid form;
   wherein the compacted form obtained in step b) comprises the surface-reacted calcium carbonate of step a); and
   wherein the method further comprises mixing the granules with at least one formulating aid selected from the group consisting of a lubricant, an impact modifier, a plasticizer, a wax, a stabilizer, a pigment, a coloring agent, a scenting agent, a taste masking agent, a flavoring agent, a sweetener, a mouth-feel improver, a diluent, a film forming agent, an adhesive, a buffer, an adsorbent, an odor-masking agent and mixtures thereof.

2. The method according to claim 1, wherein the natural ground calcium carbonate comprises a calcium carbonate containing mineral selected from the group consisting of marble, chalk, dolomite, limestone and mixtures thereof; and
   wherein the precipitated calcium carbonate comprises a precipitated calcium carbonate having aragonitic, vateritic or calcitic mineralogical crystal forms and mixtures thereof.

3. The method according to claim 1, wherein the surface-reacted calcium carbonate
   i) has a BET specific surface area of from 20 $m^2/g$ to 450 $m^2/g$ measured using the nitrogen and BET method according to ISO 9277; and/or
   ii) comprises particles having a volume median grain diameter $d_{50}$ of from 1 μm to 50 μm; and/or
   iii) has an intra-particle intruded specific pore volume within the range of 0.15 $cm^3/g$ to 1.35 $cm^3/g$ calculated from a mercury intrusion porosimetry measurement.

4. The method according to claim 1, wherein roller compacting step b) is carried out at a roller compaction pressure in the range from 1 kN/cm to 28 kN/cm.

5. The method according to claim 1, wherein sieving step d) is carried out by sieving with a mesh having a size selected from the group consisting of 180 μm, 250 μm, 355 μm, 500 μm and 710 μm.

6. The method according to claim 1, wherein the granules are mixed with a disintegrant.

7. The method according to claim 1, wherein the at least one active ingredient and/or inactive precursor thereof is selected from the group consisting of a fragrance, a flavour, a herbal extract a fruit extract, a nutrient, a trace mineral, a repellent, food, a cosmetic, a flame retardant, an enzyme, a macromolecule, a pesticide, a fertilizer, a preserving agent, an antioxidant, a reactive chemical, a pharmaceutically active agent, a pharmaceutically inactive precursor of synthetic origin, a pharmaceutically inactive precursor of semi-synthetic origin, a pharmaceutically inactive precursor of natural origin thereof, and mixtures thereof.

8. The method according to claim 1, further comprising a final step of tableting or filling the loaded granules into capsules.

9. The method according to claim 1, wherein the at least one active ingredient and/or inactive precursor thereof is provided in a solvent selected from the group consisting of water, methanol, ethanol, n-butanol, isopropanol, n-propanol, n-octanol, acetone, dimethylsulphoxide, dimethylformamide, tetrahydrofurane, a vegetable oil, a derivative of a vegetable oil, an animal oil, a derivative of an animal oil, a molten fat, a wax, and mixtures thereof.

10. The method of claim 1, wherein the compacted form obtained in step b) consists essentially of the surface-reacted calcium carbonate of step a).

11. The method according to claim 1, wherein sieving step d) is carried out.

12. The method according to claim 1, wherein the compacted form obtained in step b) does not comprise a formulating aid.

13. The method according to claim 1, wherein the compacted form obtained in step b) does not comprise a binder or disintegrant.

14. The method according to claim 1, wherein the compacted form obtained in step b) does not comprise an active ingredient and/or inactive precursor thereof.

* * * * *